United States Patent
Van Boom et al.

(10) Patent No.: US 6,852,892 B2
(45) Date of Patent: Feb. 8, 2005

(54) PROCESS FOR THE SYNTHESIS OF SPHINGOSINE

(75) Inventors: Jacobus Hubertus Van Boom, Oegstgeest (NL); Richard Jan Baptist Henrikus Nouel Van den Berg, Oegstgeest (NL)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 10/325,279

(22) Filed: Dec. 20, 2002

(65) Prior Publication Data

US 2003/0171621 A1 Sep. 11, 2003

(30) Foreign Application Priority Data

Dec. 20, 2001 (EP) .................................. 01205093

(51) Int. Cl.$^7$ .......................................... C07C 209/68
(52) U.S. Cl. ...................... 564/503; 564/468; 564/507; 564/509
(58) Field of Search ................. 564/468, 503, 564/507, 509

(56) References Cited

FOREIGN PATENT DOCUMENTS

WO    WO 95/12683    5/1995

OTHER PUBLICATIONS

Shapiro, David and Khyaim Segal. "The Synthesis of Sphingosine", J. Amer. Chem. Soc. (1954), vol. 76, p 5894–5.

Wild, Robert and Richard R. Schmidt. "Sphingosine and Phytosphingosine from D–Threose Synthesis of a 4–Keto–Ceramide", Tetrahedron: Asymmetry, vol. 5 No. 11, pp. 2195–2208, 1994.

Koskinen, Paivi M. and Ari M.P. Koskinen. "Sphingosine, and Enigmatic Lipid: A Review of Recent Literature Syntheses", Synthesis, vol. 8, p 1075–1091.

Gargano, Joseph M. and Watson J. Lees. "Synthesis of an orthogonally protected D–(+)–erythro–sphingosine", Tetrahedron Letters 42 (2001), pp. 5845–5847.

Compostella, Federica, Laura Franchini, Luigi Panza, Davide Prosperi and Fiamma Ronchetti. "A formal synthesis of 3–0–4–(4–methoxybenzyl)–azidosphingosine by a modified Julia olefination", Tetrahedron 58 (2002). Italy, Apr. 11, 2002.

Primary Examiner—Brian J. Davis
(74) Attorney, Agent, or Firm—Scully, Scott, Murphy & Presser

(57) ABSTRACT

This invention relates to a method for the production of a sphingoid base according to formula

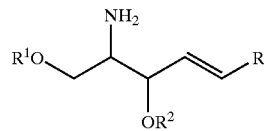

comprising the steps of
(1) dissolving a starting compound according to formula III or a salt thereof in a substantially inert solvent,

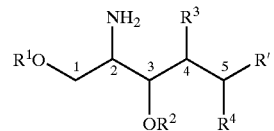

(2) protecting the NH$_2$ group with a NH$_2$ protecting group,
(3) activating the C-4 HR$^3$ group for an elimination reaction with the C-5 HR$^4$ group,
(4) causing an elimination reaction to take place to form a double bond between the C-4 and C-5 carbon atom, and
(5) removing the NH$_2$ protecting group.

24 Claims, No Drawings

PROCESS FOR THE SYNTHESIS OF SPHINGOSINE

FIELD OF THE INVENTION

The present invention relates to sphingolipids, and more particularly to a method for the production of a sphingoid base.

BACKGROUND OF THE INVENTION

Glycosphingolipids are important components of plasma membranes and such lipids play an important role in numerous biological processes, including cellular recognition processes and numerous signal transduction pathways. A vast number of naturally occurring glycosphingolipids are characterized by the presence of D-erythro-sphingosine, the primary hydroxyl group of which is glycosylated while the amino function is acylated by a fatty acid, thus constituting a ceramide unit.

In recent years, glycosphingolipids are gaining interest for cosmetic, pharmaceutical and therapeutic applications.

Although various lipids have been found to play a role in stratum corneum homeostasis, ceramides are assumed to be the main lipid components within the intercellular lipid membranes for holding the corneocytes together, and ceramides tend to be essential components in building and maintaining the barrier function of the stratum corneum. The observation that topical application of ceramides improves the barrier function of the stratum corneum as well as the moisture retaining properties of the skin, amongst others, account for this increasing interest. Besides improving the function of the stratum corneum, topical application of ceramides has been found to assist in repairing damaged epidermal barrier function. Following these observations, a wide variety of cosmetic and pharmaceutical products containing sphingoid bases, ceramides and glycosphingolipids have been developed.

Initially, sphingolipids for cosmetic and pharmaceutical applications were obtained by extraction of animal tissue. However, the thus obtained sphingolipids are a heterogenous mixture of a plurality of structurally different sphingolipids, which are potentially unsafe due to the possible presence of hazardous micro-organisms. Besides this, extraction from tissue is a laborious and expensive method, with a low yield. In order to meet the growing demand for sphingolipids, numerous attempts have been made to develop synthetic pathways for producing sphingolipids and their sphingoid base building blocks.

A structural unit common to ceramide 1, 1a, 2, 4, 5 is D-erythro-sphingosine (see formula 1 below). Examples of synthetic pathways to sphingosine are disclosed, for example, in Shapiro D. et al, J. Am. Chem. Soc. 1954, 76, 5897–5895, Lees W. J. Tetrahedron Letters, 2001, 42, 5845–5847, Compostella et al., Tetrahedron Letters, 2002, 58, 4425–4428.

In P. M. Koskinen, Synthesis 1998, 8, 1075–1091 several chemical synthetic routes for the synthesis of sphingosine are disclosed. One of the main issues in developing a suitable chemical process appears to be the problem of obtaining sphingosine in its naturally active configuration, i.e., D-erythro-sphingosine. To achieve this, synthesis was started from chiral starting products. Chirality was introduced in subsequent reaction steps through catalysis, or a chiral auxiliary was added in case non-chiral compounds were used as starting compounds. However, all these chemical synthesis routes have in common that the routes involve a large number of reaction steps, which often provide a low yield, a low trans/cis selectivity of the olefinic bond and a low stereo specificity.

In R. Wil et al, Tetrahedron Asymmetry, 1994, 2195–2208 a method is disclosed for a stereoselective synthesis of D-erythro-sphingosine, starting from D-galactose. This prior art method however comprises a large number of subsequent reaction steps, several of them giving incomplete conversion and a low selectivity to the desired product. In this prior art chemical synthesis method, the key Grignard reaction for elongating 2,4-O-benzylidene-D-threose into the desired D-arabino configurated sphingosine precursor gave poor diastereo selectivity. Mesylation of this precursor favors the C-2 OH group, which is subsequently subjected to azide substitution to give a D-ribo phytosphingosine derivative. The 4,5-trans double bond is introduced by coupling a p-nitrobenzenesulfonyl moiety to the 4-hydroxyl group of the D-ribo phytosphingosine derivative, and subjecting this coupled compound to a base induced elimination reaction, which favors the formation of the 4,5 sphingosine double bond. Two further reaction steps finally gave the desired D-erythro-sphingosine.

Phytosphingosine, another sphingoid base, in contrast to sphingosine, is commercially available on an industrial scale. A biotechnological process for the production of phytosphingosine by mutant yeast strains is disclosed, for example, in EP-A-726.960.

SUMMARY OF THE INVENTION

There is thus a need to provide sphingolipids, in particular sphingoid bases such as sphingosine and phytosphingosine as well as the ceramides based on these compounds, in commercially acceptable amounts using a cost effective method. Therefore, it is an object of the present invention to provide an economically feasible process for the production of sphingoid bases, in particular a process for the production of sphingosine, more particularly D-erythro-sphingosine (1), starting from phytosphingosine (2), to be used on an industrial scale.

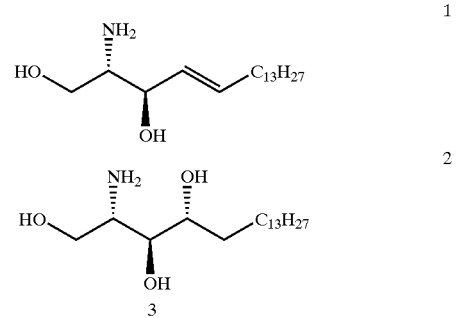

Sphingoid bases that are compatible with human tissue in general correspond to the formula below:

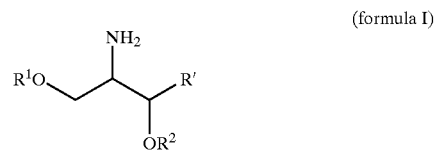

in which

R' is a hydrocarbon chain having 7–52, preferably 15–21, carbon atoms, which may be a straight chain or branched, saturated or contain one or more double bonds, and which may contain one or more functional groups, the functional groups being preferably selected from a hydroxyl group, an alkoxy group, a primary, secondary or tertiary amine, a thiol group, a thioether or a phosphorous containing functional group, a ketone, or an ester residue. Preferably, however, the functional group is a OH-group. In case R' is branched, the side chains preferably contain 1–4 carbon atoms, more preferably the side chains comprise a methyl group.

$R^1$ and $R^2$ may be the same or different and may be H or a hydrocarbon chain having 1–10, preferably 1–5, carbon atoms, which may be a straight chain or branched, saturated or contain one or more double bonds, and which may contain one or more functional groups. Preferably however, $R^1$ and $R^2$ are H.

The present invention concerns a process for the production of a sphingoid base, which is a preferred embodiment of the above given formula. In particular, the present invention concerns a method for the production of a sphingoid base according to formula II

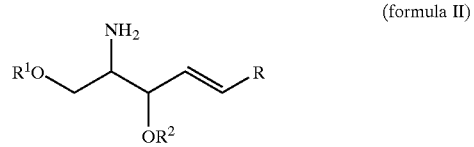

(formula II)

in which

R is a hydrocarbon chain having 5–50, preferably 13–19, carbon atoms, which may be a straight chain or branched, saturated or contain one or more double bonds, which may contain one or more functional groups, the functional groups being preferably selected from a hydroxyl group, an alkoxy group, a primary, secondary or tertiary amine, a thiol group, a thioether, a phosphorous containing functional group, a ketone, or an ester residue; and $R^1$ and $R^2$ may be the same or different and may be H or a hydrocarbon chain having 1–10, preferably 1–5, carbon atoms, which may be a straight chain or branched, saturated or contain one or more double bonds, which may contain one or more functional groups, as mentioned above.

An economically feasible process for the production of the sphingoid base of formula II may be obtained by using, as a starting compound, the organic base of formula III below and subjecting this compound to a process comprising the steps of:

(1) dissolving a starting compound according to formula III or a salt thereof in a substantially inert solvent,

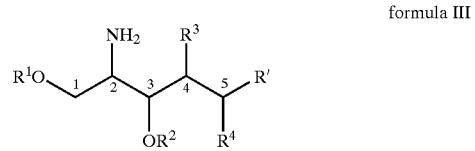

formula III in which $R^1$, $R^2$, are as defined above $R^3$ and $R^4$ may be the same or different and may be H, OH, or a hydrocarbon chain having 1–10, preferably 1–5, carbon atoms, which may be a straight chain or branched, saturated or contain one or more double bonds, and which may contain one or more functional groups, and R' is a hydrocarbon chain having 3–48, preferably 11–17, carbon atoms, which may be a straight chain or branched, which may be saturated or contain one or more double bonds, which may contain one or more functional groups, the functional groups being preferably selected from the group of a hydroxyl group, an alkoxy group, a primary, secondary or tertiary amine, a thiol group, a thioether or a phosphorous containing functional group, a ketone, an ester residue, (2) protecting the $NH_2$ group with a $NH_2$ protecting group,
(3) activating the C-4 $HR^3$ group for an elimination reaction with the C-5 $HR^4$ group,
(4) causing an elimination reaction to take place to form a double bond between the C-4 and C-5 carbon atoms, and
(5) removing the $NH_2$ protecting group. The removal step may be done immediately, as part of the process, or later on after having stored the compound for some period of time.

In the process of the present invention, care is taken to first protect the $NH_2$ function with a protecting group and to thereafter carry out the activation of the C-4 $HR^3$ for the elimination reaction with C-5 $HR^4$ only thereafter. This is done to allow separately controlling the reactions occurring on both the C-4 $HR^3$ and $NH_2$ sites. This is of particular importance in case one or more of $R^1$, $R^2$, is a hydrogen and $R^3$ is an OH group, as the OH protecting groups used with the present invention have been found to be also reactive to the amine function.

The starting compound used in the method of the invention is preferably a sphingoid base or a derivative. Specifically, the starting compound used in the present invention is a compound coresponding to formula IV or a salt thereof

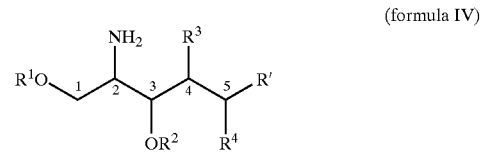

(formula IV)

in which $R^1$, $R^2$ and $R^4$ are as defined above;

$R^3$ may be H, OH, or a hydrocarbon chain having 1–10, preferably 1–5, carbon atoms, which may be a straight chain or branched, saturated or contain one or more double bonds, and which may contain one or more functional groups; and $OR^3$ may further be an O-alkyl group, an O-allyl, an ester, an O-sulfoxide, an O-sulphonyl group, a halogen, an O—S-alkyl group, a Se—R group, a S-peroxide group, a Se—R group, a CH—Se—R, or a CH—SeO—R group.

More preferred starting compounds include those corresponding to formula (V):

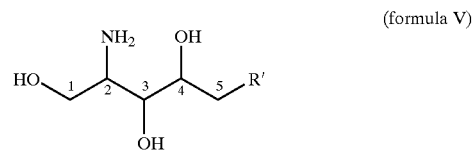

(formula V)

in which R' is as defined above.

The preferred compounds of formula IV and V are those having the D-ribo configuration, as this is the stereochemical configuration that is most abundant in the stratum corneum. The compounds of formula (IV) and (V) may however also take the D-threo configuration or any other configuration known to one skilled in the art.

More preferably as a starting compound use is made of sphinganine, phytosphingosine, monoacetylphytosphingosine, tetra-acetyl-phytosphingosine, monoacylphytosphingosine or a derivative or a salt thereof. Phytosphingosine is the most particularly preferred starting product as the compound is commercially available.

When using phytosphingosine or a derivative or a salt thereof as a starting compound, the process of the invention comprises the steps of:

(1) protecting the $NH_2$ group with a $NH_2$ protecting group,
(2) thereafter protecting the C-1 OH group with a protecting group selective to the C-1 OH group,
(3) protecting the C-3 OH group with a protecting group selective to the C-3 OH group,
(4) activating the C-4 OH for an elimination reaction with C-5H,
(5) causing an elimination reaction to take place to form a double bond between the C-4 and C-5 carbon atoms,
(6) removing the OH protecting groups followed by removing the $NH_2$ protecting group.

When using sphinganine or a derivative or a salt thereof as a starting compound, the process of the present invention comprises the steps of:

(1) protecting the $NH_2$ group with a $NH_2$ protecting group,
(2) thereafter protecting the C-1 OH group with a protecting group selective to the C-1 OH group
(3) oxidizing the C-3 OH to a C=O,
(4) rearranging the C=O to the corresponding allylic ketone,
(5) reduction of the ketone function of the allylic ketone into an allylic alcohol,
(6) removing the OH protecting groups followed by removing the $NH_2$ protecting group.

Protection of the $NH_2$ group may be achieved in different ways according to the preferred embodiments describe below.

DETAILED DESCRIPTION OF THE INVENTION

First Preferred Embodiment.

According to a first preferred embodiment of the present invention, the organic base of formula III is used as the starting product and subjected to a diazo transfer reaction to produce the corresponding azide compound. The process comprises the steps of:

(1) dissolving an amount of the compound of formula II in a substantially inert solvent,
(2) making the compound of formula II react with an azide reactant in a so-called diazo transfer reaction, the azide reactant corresponding to the formula $R^5$—$N_3$ in which $R^5$ is an electron withdrawing group.

The reaction scheme may be summarized as follows:

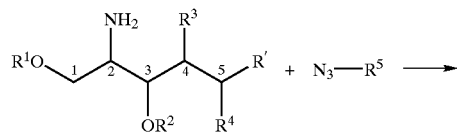

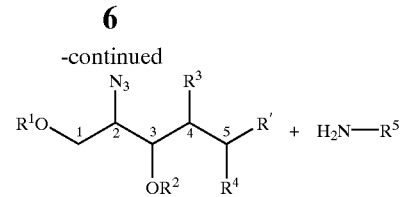

Converting the $NH_2$ group into an azide allows minimizing the risk to racemization of the mixture and maintaining the optical activity at the asymmetric carbon atom carrying the $NH_2$ group. This is surprising, as azide substitution reactions are usually not stereo selective and may either involve a partial or total racemization, following partial or total inversion of the optical activity. The retained stereospecificity is important as typically only one of the stereo isomers of biologically important molecules shows biological activity, whereas the other stereo isomer is mostly biologically inactive.

The solvent for the diazo transfer reaction may be any suitable solvent known to one skilled in the art. The solvent is preferably selected from the group of water, alcohols, ethers, esters, ketones, sulfoxides, amides, halogen containing alkanes, nitriles (e.g., methanol, DMSO, DMF, dichloromethane, tetrahydrofuran, acetonitrile), as the solubility of phytosphingosine in these solvents, in particular in methanol and acetonitrile, has been found to increase with temperature.

The azide used in the method of the present invention is an activated azide, in which $R^5$ is an electron-withdrawing group. The preferred azide corresponds to the formula (VI)

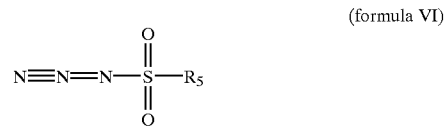

(formula VI)

wherein $R^5$ is an electron withdrawing substituent, preferably selected from the group of an alkyl group having 1–6 carbon atoms, a halogen atom, F, Cl, Br, a halogenated methyl or ethyl group, preferably $CF_3$-(triflyl), $CF_2CF_3$-(tesyl), an aryl group, a phenyl group, a phenyl group containing one or more substituents, for example, $NO_2$, methyl group (Ts), carboxyl group.

The use of phytosphingosine as the starting product, as well as the other bases of formula I, III, IV involves the problem that these compounds have a low solubility in the majority of the frequently used solvents for organic reactions. With the present invention, it has surprisingly been found that by addition of the sulfonyl azide reactant, the solubility of phytosphingosine azide product in these solvents may be significantly improved. As a result of this improved solubility, the diazo transfer reaction may be performed at rather high yields approaching virtually complete conversion. Besides this, the diazo transfer reaction product of phytosphingosine appears to be a solid product, which can be easily recovered from the reaction mixture in good yield and high purity.

The applicants of the present invention are of the opinion that the observed stereo selectivity of the diazo transfer reaction of the present invention can be explained in that the free electron pair of the nitrogen atom of the $NH_2$ group of phytosphingosine has a higher nucleophilic character than the free electron pair on the terminal or central nitrogen of the sulfonyl azide reactant. As a consequence, the $NH_2$ group of the phytosphingosine will act as the nucleophilic group in the diazo transfer reaction instead of the azide functionality, which results in maintaining stereospecificity of the phytosphingosine.

The fact that the azide acts as the electrophilic reagent is unexpected. The nature of azide functionalities has been found to be rather unpredictable, and may either be nucleophilic or electrophilic in character. The fact that the azide reactant acts as the electrophilic reagent is conspicuous. The azide group has been found to show a good stability in widely varying reaction conditions, although it is advised to minimize the occurrence of reductive reaction conditions as much as possible. Moreover, the azide group appears to activate the C-1 OH group, thus rendering the azide compound of this specific composition of particular interest as a starting product for the preparation of further products.

For safety reasons, the activated azide is preferably generated in situ by reaction of a sulfonyl compound of formula VII

(formula VII)

with $MN_3$, M being a monovalent cation, preferably selected from the group of alkali metal ions. In formula VII, $R^5$ is an alkyl residue or an electron withdrawing group, preferably selected from the group of an alkyl group having 1–6 carbon atoms, a halogen atom, F, Cl, Br, a halogenated methyl or ethyl group, preferably $CF_3$-(triflyl), $CF_2CF_3$-(tesyl), an aryl group, a phenyl group, a phenyl group containing one or more substituents, for example, $NO_2$, methyl group (Ts), carboxyl group and X is a halogen atom or a group responding to the formula (VII)

(formula VIII)

wherein $R^6$ is, independently of $R^5$, an alkyl residue or an electron withdrawing group, preferably selected from the group of an alkyl group having 1–6 carbon atoms, a halogen atom, F, Cl, Br, a halogenated methyl or ethyl group, preferably $CF_3$-(triflyl), $CF_2CF_3$-(tesyl), an aryl group, a phenyl group, a phenyl group containing one or more substituents, for example $NO_2$, methyl group (Ts), carboxyl group M is a monovalent cation preferably selected from the group of alkali metal ions.

Preferably the sulfonyl azide compound is generated in situ by causing a sulfonic anhydride

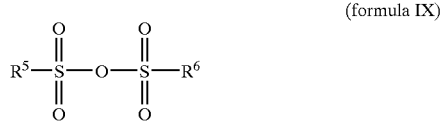

(formula IX)

to react with an azide anion $MN_3$.

The preferred sulfonic anhydrides include those of formula (IX) in which $R^6$ and $R^7$ are strong electron withdrawing groups, for example trifluoromethane sulfonic anhydride.

The diazo transfer reaction may be carried out in a manner generally known to one skilled in the art, such as disclosed in Helv. Chim. Acta 1991, 74, 2073. Triflyl azide may be prepared by dissolving sodium azide in water followed by the addition of dichloromethane and trifluoromethane sulfonic anhydride. After the appropriate reaction time, triflyl azide may be extracted from the biphasic mixture. After dissolving the sphingoid base in a homogenous mixture of dichloromethane, methanol and water and adding a divalent first row d-block metal, triflyl azide was added. Sphingoid azide was found to crystallize in the course of the reaction.

The applicants of the present invention have found that the sphingoid azide compound, in particular phytosphingosine azide, is a very suitable starting product for the direct production of an organic base with a C-4-C-5 double bond, in particular D-erythro-sphingosine.

To minimize the risk to reaction of the C-1 OH group in the course of the process, this group is coupled to a protection group. Thereby, care is taken to select a compound which selectively reacts with the C-1 OH group. Mostly however, the $NH_2$ function will be converted first, as the protective groups for OH functions are also reactive to the $NH_2$. However, it may also be desirable to simultaneously protect the C-1 and C-3 OH groups. It is however important that the OH protecting groups are selected such that they are substantially inert to the elimination reaction between the C-4 OH and the C-5H group. It is also important that the C-4 OH protecting group is capable of activating this group for elimination with the C-5H as an elimination reaction at this bond should be favored and the risk to all other elimination reactions should be minimized.

As soon as the elimination reaction has taken place and the double bond between the C-4 and C-5 has been formed, all protecting groups may be removed.

When simultaneously protecting the C-1 and C-3 OH group, the $NH_2$ protected compound is caused to react with a compound selected from a silylating agent compound with at least two groups reactive with OH, although an acetal or ketal protecting group may also be used. These reagents include an aldehyde RCHO, a ketone RCOR' in which R and R' may be the same or different and preferably comprise an alkyl group having 1–20 carbon atoms, straight chain or branched, aromatic, containing functional groups such as, for example, $NO_2$ or $CH_3$ or not. When using the silylating agent a six membered ring is formed with the C-1 and C-3 OH group. In that way, the C-1 and C-3 OH groups may simultaneously, temporarily be protected against further reaction.

Preferred silylating agents include compounds according to formula X

(formula X)

in which $R^{10}$ and $R^{11}$ independently of each other have 1–35 carbon atoms, the alkyl group being a straight chain or branched. X is a halogen, preferably a chloride residue or O-triflyl or a F containing group.

Preferred silylating compounds comprise at least two reactive sites towards the 1,3-diol function, so that a six-ring member is formed upon reaction with the C-1 and C-3 phytosphingosine OH groups. The formation of the six membered ring namely renders the molecule more rigid, thus assisting in promoting the elimination reaction at a later stage at the C-4-C-5 bond. In case the elimination reaction is carried out in the presence of a N-substitued base, there is namely a risk that this N-containing base involves a substitution reaction at the C-4 position.

Preferred silylating agents for use in the present invention include di-alkyl silylene compounds for example di-t-butylsilylenedicholoride, di-isopropylsilylenedichloride or ditriflate reagents thereof. These reactions are preferably carried out at a temperature of between 233K and 373K.

Removing of the dialkylsilylene group after termination of the elimination reaction is done through addition of a fluoride donor or by acid treatment of the silylated product, as is generally known by one skilled in the art. For general deprotection protocols, see "Protective groups in organic synthesis", third edition, T. W. Green, P. G. M. Wuts, 1999, pg 237–238. Removing of the azido function in step (7) is done according to the methods generally known to one skilled in the art. Thereto, the reaction mixture is subjected to reductive reaction conditions. Examples of suitable reducing agents include $H_2S$ in pyridine or any other compound with reductive properties known to one skilled in the art.

Activation of the C-4 OH for the subsequent elimination reaction is achieved by coupling the C-4 OH group to the sulfonyl compound of formula VII defined above:

(formula VII)

The use of a sulfonyl compound is preferred, as it is capable of selectively activating the C-4 OH group. Surprisingly, leaving of the sulfonyl group appears to be associated with an β-elimination reaction, involving the simultaneous formation of the (sphingosine) double bond between the C-4 and —C-5 carbon atoms. The elimination reaction appears to take place with virtually complete selectivity towards the desired end product, which appeared to be virtually free of unwanted side products.

Depending on the nature of the $R^5$ or $R^6$ functional group, in particular the electronegativity and steric hindrance thereof, the group may exert a better or smaller polarization effect to the C-4 O bond. The better the polarization, the faster the subsequent elimination reaction will take place. Therefore, the preferred $R^5$ or $R^6$ functional groups include alkyl residue having 1–6 carbon atoms, $CF_3$, $CCl_3$, a phenyl residue, a phenyl residue substituted with an electron withdrawing group, for example $NO_2$ (Ns), methyl group (Ts), carboxyl group.

In particular, activating of the C-4 OH by trifluoromethane sulfonyl is preferred, as this activation involves a direct elimination reaction and formation of the sphingosine trans double bond. The triflate group has been found capable of involving an intense activation of the C-4 O bond, followed by a fast elimination reaction. The applicants of the present invention are of the opinion that this may be explained by the fact that the triflate derivative is an unstable molecule, as a consequence of which the activated OH group leaves the molecule almost instantaneously to improve the stability of the molecule. This entails the advantages that an almost instantaneous elimination reaction takes place and that no additional reaction step has to be provided for removing the sulfonyl group.

Another preferred C-4 activating group includes the group of xanthate esters O—C(=S)—S-Me, which may be removed through addition of a radical reaction or thermolysis. Removing the C-1 and C-3 protecting group then gives azidosphingosine. In the later process sphingosine is obtained.

The temperature at which reaction steps (3) and (4) are carried out will in general vary between 233K and 353 K, and will be selected by one skilled in the art, taking into account the nature of the protecting group.

Depending on the nature of the C-4 OH elimination inducing group, the elimination reaction which is carried out in the presence of a strong organic hindered base, will be carried out at a lower temperature to allow removal of the sulfonyl group and simultaneously the elimination reaction to form the trans double bond. Introduction of steric hindrance allows minimizing the risk to unwanted side reactions in the course of the elimination reaction. This has a positive influence to the selectivity of the reaction. It is however also possible to carry out the reaction at somewhat higher temperatures.

The above described reaction steps are preferably carried out in a solvent selected from the group of tetrahydrofuran, methanol, dichlormethylmethane, DMF, DMSO, acetonitrile, and pyridine.

Second Preferred Embodiment.

According to a second preferred embodiment of the present invention, to prevent it from undergoing unwanted reactions, in step (2), the $NH_2$ functionality in the compound of formula I or III is converted to an amide, a cyclic amine, an imine, an azide, an oxazoline, a carbamate group, (e.g. N—BOC group, a Fmoc group or a Z group). The latter are frequently used N-protecting groups.

Protection of the $NH_2$ may be achieved by causing the compound of formula I or III to react with a compound selected from the group comprising an organic acid of formula $R^8COOH$, for example, a fatty acid, this reaction having the nature of an acid coupling reaction; an ester $R^8COOR^9$, therein preferably $R^9$ is an electron withdrawing group to have an activated ester, for example, p-nitrophenyl; an acid anhydride $R^8CO$—O—$COR^9$ may also be used although this compound appears to be more expensive; an organic acid halogenide $R^8COX$, for example, benzoylchloride, is also suitable although the selectivity towards selective reaction with $NH_2$ may sometimes be insufficient as these types of compounds are also reactive towards OH; or di-tert-butyldicarbonate. Particularly preferred is di-tert-butyldicarbonate as it allows obtaining a compound with a N—BOC protected $NH_2$ group which may be easily removed by acidolysis. When using the Z group as a protecting group, in the course of its removal in reductive circumstances, there is a risk to hydrogenation of the sphingosine double bond.

These compounds are preferred as they have a high selectively towards reaction with the $NH_2$, leaving the OH groups unaffected. The above mentioned compounds allow protecting the $NH_2$ group against undesired reactions in this process without affecting the stereospecificity at the nitrogen carbon atom.

In subsequent step (2) and (3), the C-1 and C-3 OH groups may be protected as described above for the first embodiment.

The compound with the N—BOC protected $NH_2$ group and the protected C-1, C-3 OH groups is activated for elimination in reaction step (3).

This is preferably done by first converting the C-4 OH group into a ketone, thereafter applying circumstances such that the keto-enolate equilibrium is established and converting the OH of the enol into a good leaving group. The preferred leaving group is a sulfonyl group, preferably a triflate group. This procedure further allows minimizing the risk of reaction of the N of the N—BOC protected $NH_2$ with the reactants needed to form the good leaving group.

The oxidation reaction may be carried out as is generally known to one skilled in the art. The keto-enol equilibrium is achieved by treatment of the ketone derivative with a strong base such as for example alkali bisalkylamide, or potassium bis(trimethylsilylamide), butyllithium. The OH group of the enol may now be caused to react with a sulfonyl compound of formula VI above.

The sulfonyl group is preferably removed through reductive elimination in the presence of a hydrogenation catalyst, for example, a Pt. Pd or Rh catalyst.

Third Preferred Embodiment.

According to a third preferred embodiment of the present invention, the compound of formula III is caused to react with an organic acid, an activated ester, an acid halogenide, an acid anhydride, to convert the amine function to the corresponding amide. Particularly preferred is the acid halogenide according to formula XI

(formula XI)

in which $R^{12}$ may be a hydrocarbon group having 1–50 carbon atoms, which may be a straight chain or branched, saturated or contain one or more unsaturated bonds, cyclic, aromatic, and contain functional groups, for example, OH, SH etc. The advantage is that the risk to inversion of the optical activity at the C-2 position may be minimized, this compound showing a high selectivity towards reaction with the $NH_2$ group.

In a first instance, the acid halogenide will react with the $NH_2$ group.

A preferred acid halogenide is benzoyl chloride or acetyl chloride as this allows formation of a stable amide bond.

For the protection of the C-1 OH group, this group is activated by a sulfonyl reagent as shown in formula VII, allowing an intramolecular reaction with the amide bond to form a five memebered 2-substituted oxazoline. For example for benzoylamide this will give the 2-phenyl-oxazoline and the acetylamide will give 2-methyl-oxazoline.

When proceeding with the reaction, it is important to ensure that the risk to inversion of the optical activity at the C-3 is also minimized. In particular, it should be ensured to counteract reaction between the $NH_2$-benzoyl group and the C-3 OH and the C-4 OH, which is favorable as it gives rise to the formation of a 5 membered ring, as such reaction would involve inversion of the optical activity at the C-3, or rendering the C-4 OH less suitable for the desired elimination reaction. This object may be achieved by a careful selection of the protecting groups for the C-3 OH and C-4 OH functional groups.

After having coupled the $NH_2$ and C-1 OH group to the protective group as a 2-substituted oxazoline, the C-3 OH and C-4 OH are converted into an epoxide. This may be done trough epoxidation by first sulfonylating the OH group followed by application of alkaline conditions or by converting the C-3 OH and C-4 OH to an ortho ester, for example, by causing it to react with trimethylorthoformate, followed by a substitution with TMSX or AcX in which X is a halogen and applying strong alkaline conditions to induce saponication of the formed ester followed by the subsequent epoxide formation.

This may also be achieved by first converting the C-4 OH group into a good leaving group as has been described above and by converting the leaving group into an epoxide in the presence of a strong base, in particular a sterically hindered base so as to avoid nucleophilic substitution reactions.

Formation of the epoxide has the advantage that inversion of the optical activity at the C-3 carbon atom may be minimized, by making a particular choice of ring opening reactants. This may be achieved by causing the epoxide to react with TMSX in which X is a halogen or triflate, preferable iodine, followed by strong base treatment involving the simultaneous formation of the (sphingosine) double bond between the C-4 and C-5 carbon atoms. Surprisingly, leaving of the halogen or sulfonyl group appears to be associated with an β-elimination reaction, involving the simultaneous formation of the (sphingosine) double bond between the C-4 and C-5 carbon atoms. The elimination reaction appears to take place with virtually complete selectivity towards the desired end product, which appeared to be virtually free of unwanted side products.

Subsequent protic acid treatment followed by alkaline treatment give D-erytho-sphingosine as a pure and sole product.

The present invention is further illustrated in the following examples.

Analytical methods.

General Methods and Materials.

$^1H$ NMR and $^{13}C$ NMR spectra were recorded with a Bruker WM-200 (200/50.1 MHz), Bruker WM-300S (300/75.1 MHz) spectrometer. $^1H$ and $^{13}C$ chemical shifts are given in ppm (δ) relative to tetramethylsilane (δ=0.00), $CDCl_3$ (δ=77.00) as internal standard. Electrospray mass-spectra were recorded using a Perkin-Elmer SCIEX API 165 Single Quadruple LC/MS instrument. Dichloromethane, pyridine, tetrahydrofuran, toluene was dried by molecular sieves (4A). Column chromatography was performed on Silica gel 60 (220–440 mesh ASTM, Fluka). TLC-analysis was performed with silica gel TLC-plates (Merck, Silica gel, $F_{254}$) with detection by UV-absorption (254 nm) where applicable and charring (±140° C.) with 20% $H_2SO_4$ in MeOH or ammonium molybdate (25 g/L) and ceric ammonium sulfate (10 g/L) in 20% $H_2SO_4$. Compounds containing $NH_2$-functions were visualized by spraying TLC-plates with a solution of ninhydrin (0.30 g) in n-butanol (100 mL) containing acetic acid (3 mL) followed by charring ±140° C. Prior to reactions that require anhydrous conditions, traces of water were removed by co-evaporation with dry toluene. These reactions were conducted under dry argon atmosphere.

EXAMPLE 1

Preparation of (2S,3S,4R)-2-azido-1,3,4-octadecanetriol

Preparation of Triflyl Azide ($TfN_3$).

$NaN_3$ (19.8 g, 0.305 mol) was dissolved in water (50 mL) and cooled to 273K. After the addition of DCM (50 mL) the mixture was stirred for 15 min, $Tf_2O$ (10.7 mL, 0.063 mol) was dropwise added over a period of 15 min, maintaining the solution at 273K. The reaction mixture was stirred for 2 h at 273K, then the mixture was extracted with DCM (2×30 mL) and washed with aqueous saturated $Na_2CO_3$ (2×30 mL). The organic layer was saved for the diazo transfer reaction.

Diazo Transfer Reaction.

Phytosphingosine (9.8 g, 30.9 mmol) was dissolved in warm (±308K) MeOH (300 mL), giving a clear solution. A freshly prepared solution of $K_2CO_3$ (6.4 g, 60 mmol) and $CuSO_4$ (47 mg, 0.29 mmol) in water (100 mL) was added. The clear solution became turbid. The above-prepared $TfN_3$ solution was added, yielding a homogeneous solution, which was stirred for 18 h at ambient temperature. The formed crystals where filtered and washed with cooled (273K) aqueous MeOH (2×100 mL, 1:1, v/v). The crystals where dried (vacuum oven at 333K, 18 h) yielding 9.4 g (87%) of product.

The reaction product had a melting point of 370–371K. Optical rotation: 15.1° (c=1.0, $CHCl_3$) IR: 2120 (large azido peak) ES-MS: m/z 366.5 $[M+Na]^+$, 709.6 $[2M+Na]^+$ 1H-NMR ($CDCl_3$): δ=0.88 (t, 3H, $CH_3$), 1.25 (s, H, $CH_2$), 1.56 (br. s, 4H, $CH_2$), 3.68 (m, 1H, H-2,), 3.80 (m 2H, H-3, H-4), 3.87 (dd, 1H, H-1a, $J_{1a,1b}$=11.7 Hz, $J_{1a,2}$=4.4 Hz), 4.01 (dd, 1H, H-1b, $J_{1a,1b}$=11.7 Hz, $J_{1b,2}$=5.9 Hz).

EXAMPLE 2

Preparation of (2S,3S,4R)-2-Azido-1,3-O-di-(tert-butyl)silanediyl-1,3,4-octadecanetriol To a solution of (2S,3S,4R)-2-azido-1,3,4-octadecanetriol (1.362 g, 3.97 mmol) in DMF (16 mL) at 273K was added $tBu_2Si(OTf)_2$ (1.59 mL, 4.37 mmol) dropwise over 15 min. The solution was stirred an additional 30 min, and pyridine was added (0.42 mL, 1.2 equivalents) and stirred 5 min. The solution was diluted with ethyl acetate (100 mL) and washed with aqueous $NaHCO_3$ (1×50 mL, 10%), water (3×50 mL) and dried ($MgSO_4$). Flash chromatography on silica gel with petroleum ether/ethyl acetate (100:0→75:25, v/v) produced 1.661 g (86% yield) of yellow oil.

Optical rotation: 45.20 (c=1.0, $CHCl_3$) ES-MS: m/z 484.5 $[M+H]^+$, 967.9 $[2M+H]^+$ The reaction product was characterised by NMR as follows:

$^1$H-NMR ($CDCl_3$): δ=0.88 (t, 3H, $CH_3$), 1.00 (s, 9H, tBu), 1.05 (s, 9H, tBu), 1.26 (s, H, $CH_2$), 1.52 (m, 2H, $CH_2$), 2.14 (d, 1H, OH), 3.51 (m, 1H, H-2, $J_{1eq,2}$=4.7 Hz, $J_{1ax,2}$=10.0 Hz, $J_{2,3}$=9.8 Hz), 3.75 (br. s, 1H, H-4), 3.93 (dd, 1H, H-3, $J_{3,4}$=3.7 Hz, $J_{2,3}$=9.6 Hz), 3.94 (dd, 1H, H-1ax, $J_{1ax,1eq}$=10.8 Hz, $J_{1ax,2}$=10.0 Hz), 4.22 (dd, 1H, H-1eq, $J_{1ax,1eq}$=10.8 Hz, $J_{1eq,2}$=4.7 Hz). $^{13}C\{^1H\}$-NMR ($CDCl_3$): δ=14.0 ($CH_3$), 20.1 (Cq tBu) 22.5, 25.5 (×$CH_2$), 26.9, 27.4 (2×tBu), 29.3, 29.6, 30.9, 31.8 (×$CH_2$), 58.7 (C-2), 66.1 (C-1), 72.8 (C-4), 79.0 (C-3).

EXAMPLE 3

Preparation of (2S,3S,4R)-2-Azido-1,3-O-di-(tert-butyl)silanediyl-4-O-mesyl-1,3,4-octadecanetriol

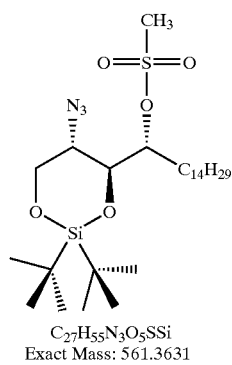

$C_{27}H_{55}N_3O_5SSi$
Exact Mass: 561.3631

Mesyl chloride (34 μL, 0.44 mmol) was added to a solution of (2S,3S,4R)-2-azido-1,3-O-di-(tert-butyl) silanediyl-1,3,4-octade-canetriol (0.195 g, 0.40 mmol) in pyridine (1 mL). After 1 h, TLC analysis indicated the complete conversion of starting material into a compound with $R_f$=0.55 (ethyl acetate/petroleum ether, 1:9, v/v). The mixture was concentrated, the residue was dissolved in diethyl ether (25 mL) washed with aqueous $NaHCO_3$ (1×20 mL, 10%), water (1×50 mL) and dried ($MgSO_4$). Flash chromatography on silica gel with petroleum ether/ethyl acetate (100:0→85:15, v/v) gave 0.217 g (96% yield) of yellow oil.

Optical rotation: 49.4° (c=1.0, $CHCl_3$)

The reaction product was characterised by NMR as follows:

$^1$H-NMR ($CDCl_3$): δ=0.88 (t, 3H, $CH_3$), 1.00 (s, 9H, tBu), 1.06 (s, 9H, tBu), 1.26 (s, H, $CH_2$), 1.56 (m, 2H, $CH_2$), 1.93 (m, 2H, $CH_2$), 3.06 (s, 3H, $CH_3$ Ms), 3.47 (m, 1H, H-2, $J_{1eq,2}$=5.1 Hz, $J_{1ax,2}$=9.5 Hz, $J_{2,3}$=10.2 Hz), 3.97 (t, 1H, H-3, $J_{2,3}$=$J_{3,4}$=10.2 Hz), 4.27 (m, 2H, $H_2$-1), 4.89 (dt, 1H, H-4, J=9.5 Hz, J=5.8 Hz, J=2.9 Hz). $^{13}C\{^1H\}$-NMR ($CDCl_3$): δ=14.0 ($CH_3$), 20.1 (Cq tBu) 22.6, 25.1 (×$CH_2$), 26.8, 27.4 (2×tBu), 28.3, 29.3, 29.6, 31.8 (×$CH_2$), 38.6 ($CH_3$ Ms), 58.3 (C-2), 66.1 (C-1), 76.4 (C-3), 82.8 (C-4).

EXAMPLE 4

Preparation of (2S,3S,4R)-2-Azido-1,3-O-di-(tert-butyl)silanediyl-4-O-tosyl-1,3,4-octadecanetriol

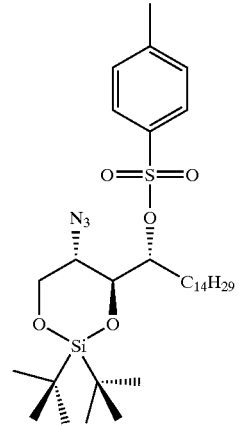

Nosyl chloride (0.187 g, 0.844 mmol) and silver p-toluenesulfonate (0.235 g, 0.844 mmol) were added to a solution of (2S,3S,4R)-2-azido-1,3-O-di-(tert-butyl) silanediyl-1,3-O-octade-canetriol (0.255 g, 0.526 mmol) in pyridine (5 mL). After stirring for 2 h at 40° C. TLC analysis indicated the complete conversion of starting material into a compound with $R_f$=0.77 (DCM/petroleum ether, 1:4, v/v). The with crystals were filtered, the filtrate was concentrated, the residue was dissolved in diethyl ether (100 mL) washed with water (1×50 mL) and dried ($MgSO_4$). Flash chromatography on silica gel with petroleum ether/DCM (100:0→75:25, v/v) gave 0.262 g (78% yield) of colourless oil.

The reaction product was characterised by NMR as follows:

$^1$H-NMR ($CDCl_3$): δ=0.88 (t, 3H, $CH_3$), 0.97 (s, 18H, 2×tBu), 1.17–1.50 (m, 26H, $CH_2$), 2.44 (s, 3H, $CH_3$ Ts), 3.34 (m, 1H, H-2, $J_{1eq,2}$=5.1 Hz, $J_{1ax,2}$=9.5 Hz, $J_{2,3}$=10.2 Hz), 3.97 (t, 1H, H-1ax, $J_{1ax,1eq}$=$J_{1ax,2}$=10.2 Hz), 4.10 (dd, 1H, H-3, $J_{2,3}$=10.2 Hz, $J_{3,4}$=2.2 Hz), 4.21 (dd, 1H, H-1 eq, $J_{1ax,1eq}$=10.2 Hz, $J_{1eq,2}$=5.1 Hz), 4.76 (dt, H-4, J=9.5, J=2.2 Hz), 7.26–7.85 (m, 4H, CH arom Ts). $^{13}C\{^1H\}$-NMR ($CDCl_3$): δ=14.0 ($CH_3$), 20.1 (Cq tBu) 21.5 ($CH_3$ Ts), 22.6, 24.8 (2×$CH_2$), 26.8, 27.3 (2×tBu), 27.7, 29.1, 29.3, 29.6, 31.9 (5×$CH_2$), 58.0 (C-2), 66.1 (C-1), 76.9 (C-3), 83.2 (C-4),127.8, 129.7 (CH arom Ts), 134.3, 144.6 (2×Cq Ts).

EXAMPLE 5

Preparation of (2S,3S,4R)-2-Azido-1,3-O-di-(tert-butyl)silanediyl-4-O-p-nosyl-1,3,4-octadecanetriol

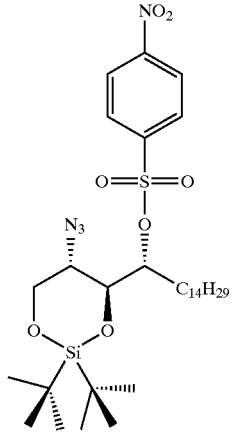

Nosyl chloride (0.163 g, 0.735 mmol) and silver triflate (0.222 g, 0.864 mmol) were added to a solution of (2S,3S,4R)-2-azido-1,3-O-di-(tert-butyl)silanediyl-1,3,4-octadecanetriol (0.270 g, 0.557 mmol) in pyridine (5 mL). After stirring for 1 h at 40° C. TLC analysis indicated the complete conversion of starting material into a compound with $R_f$=0.48 (DCM/petroleum ether, 1:4, v/v). The white crystals were filtered, the filtrate was concentrated, the residue was dissolved in diethyl ether (100 mL) washed with water (1×50 mL) and dried (MgSO$_4$). Flash chromatography on silica gel with petroleum ether/ethyl acetate (100:0→92:8, v/v) gave 0.355 g (95% yield) of colourless oil.

$^1$H-NMR (CDCl$_3$): δ=0.88 (t, 3H, CH$_3$), 0.96, (s, 9H, tBu), 0.98 (s, 9H, tBu), 1.21–1.55 (m, 26H, 13×CH$_2$), 3.39 (m, 1H, H-2, $J_{1eq,2}$=5.1 Hz, $J_{1ax,2}$=$J_{2,3}$=10.2 Hz), 3.87 (dd, 1H, H-1ax, $J_{1ax,1eq}$=11.0 Hz, $J_{1ax,2}$=10.2 Hz), 4.10 (dd, 1H, H-3, $J_{2,3}$=10.2 Hz, $J_{3,4}$=2.2 Hz), 4.24 (dd, 1H, H-1 eq, $J_{1ax,1eq}$=11.0 Hz, $J_{1eq,2}$=5.1 Hz), 4.92 (dt, H-4, J=10.2, J=2.2 Hz), 8.13–8.38 (m, 4H, CH arom Ns). $^{13}$C{$^1$H}-NMR (CDCl$_3$): δ=14.0 (CH$_3$), 20.0 (Cq tBu) 22.6 25.0, (2×CH$_2$), 26.8, 27.2 (2×tBu), 27.7, 29.0, 29.3, 29.6, 31.8 (5×CH$_2$), 58.0 (C-2), 66.1 (C-1), 77.0 (C-3), 85.2 (C-4), 124.3, 129.0 (CH arom Ns), 142.9, 150.6 (2×Cq Ns).

EXAMPLE 6

Preparation of (2S,3S,4E)-2-Azidooctadec-1,3-O-di-(tert-butyl)silanediyl-4-ene-1,3-diol

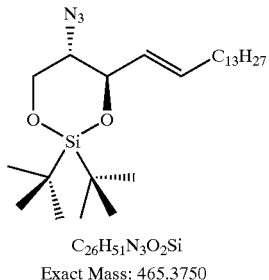

C$_{26}$H$_{51}$N$_3$O$_2$Si
Exact Mass: 465.3750

Trifluoromethanesulfonic anhydride (0.18 mL) was added under nitrogen atmosphere to a mixture of (2S,3S,4R)-2-azido-1,3-O-di-(tert-butyl)silanediyl-1,3,4-octade-canetriol (0.428 g, 0.88 mmol) in dichloroethane (5 mL) and pyridine (0.2 mL). The mixture was stirred for 16 h at ambient temperature. The reaction mixture was concentrated and the residue dissolved in diethyl ether (50 mL), washed with aqueous 10% NaHCO$_3$ (50 mL) solution. After drying on MgSO$_4$, the organic layer was concentrated in vacuo. The crude product was purified by silica gel column chromatography. Elution was performed with petroleum ether/ethyl acetate (100:0→90:10, v/v) gave 0.314 g (77%) of colourless oil.

$^1$H-NMR (CDCl$_3$): δ=0.88 (t, 3H, CH$_3$), 1.01 (s, 9H, tBu), 1.04 (s, 9H, tBu), 1.26 (s, H, CH$_2$), 2.09 (m, 2H, CH$_2$), 3.30 (m, 1H, H-2, $J_{1eq,2}$=4.4 Hz, $J_{1ax,2}$=11.0 Hz, $J_{2,3}$=9.5 Hz), 3.81 (t,1H, H-1ax, $J_{1ax,1eq}$=11.0 Hz, $J_{1ax,2}$=11.1 Hz), 4.10–4.28 (m, 2H, H-1eq, H-3, $J_{1ax,1eq}$=11.0 Hz, $J_{1eq,2}$=4.4 Hz, $J_{2,3}$=9.5 Hz, $J_{3,4}$=5.9 Hz), 5.51 (dd, 1H, H-4, $J_{3,4}$=6.6 Hz, $J_{4,5}$=15.4 Hz), 5.87 (quin. 1H, H-5, $J_{5,6a}$=6.6 Hz, $J_{5,6b}$=6.5 Hz, $J_{4,5}$=15.4 Hz). $^{13}$C{$^1$H}-NMR (CDCl$_3$): δ=14.1 (CH$_3$), 20.0 (Cq tBu) 22.7 (CH$_2$), 27.0, 27.4 (2×tBu), 28.9, 29.4, 29.7, 31.9, 32.3 (×CH$_2$), 62.5 (C-2), 66.4 (C-1), 78.1 (C-3), 129.1 (C-5), 134.7 (C-4).

EXAMPLE 7

Preparation of (2S,3S,4E)-2-Azidooctadec-1,3-O-di-(tert-butyl)silanediyl-4-ene-1,3-diol

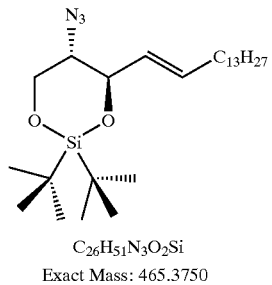

C$_{26}$H$_{51}$N$_3$O$_2$Si
Exact Mass: 465.3750

A solution of (2S,3S,4R)-2-azido-1,3-O-di-(tert-butyl)silanediyl-4-O-p-nosyl-1,3,4-octadecanetriol (0.355 g, 0.531 mmol) in toluene (5 mL) was stirred for 18 h at 100° C. with DBU (5 equivalent). The reaction mixture was concentrated and the residue dissolved in diethyl ether (50 mL), washed with aqueous 10% NaHCO$_3$ (50 mL) solution. After drying on MgSO$_4$, the organic layer was concentrated in vacuo. The crude product was purified by flash chromatography on silica gel with petroleum ether/ethyl acetate (100:0→70:30, v/v) gave 0.091 g (37% yield) of colourless oil.

$^1$H-NMR (CDCl$_3$): δ=0.88 (t, 3H, CH$_3$), 1.01 (s, 9H, tBu), 1.04 (s, 9H, tBu), 1.26 (s, H, CH$_2$), 2.09 (m, 2H, CH$_2$), 3.30 (m, 1H, H-2, $J_{1eq,2}$=4.4 Hz, $J_{1ax,2}$=11.0 Hz, $J_{2,3}$=9.5 Hz), 3.81 (t, 1H, H-1ax, $J_{1ax,1eq}$=11.0 Hz, $J_{1ax,2}$=11.1 Hz), 4.10–4.28 (m, 2H, H-1eq, H-3, $J_{1ax,1eq}$=11.0 Hz, $J_{1eq,2}$=4.4 Hz, $J_{2,3}$=9.5 Hz, $J_{3,4}$=5.9 Hz), 5.51 (dd, 1H, H-4, $J_{3,4}$=6.6 Hz, $J_{4,5}$=15.4 Hz), 5.87 (quin. 1H, H-5, $J_{5,6a}$=6.6 Hz, $J_{5,6b}$=6.5 Hz, $J_{4,5}$=15.4 Hz). $^{13}$C{$^1$H}-NMR (CDCl$_3$): δ=14.1 (CH$_3$), 20.0 (Cq tBu) 22.7 (CH$_2$), 27.0, 27.4 (2×tBu), 28.9, 29.4, 29.7, 31.9, 32.3 (×CH$_2$), 62.5 (C-2), 66.4 (C-1), 78.1 (C-3), 129.1 (C-5), 134.7 (C-4).

EXAMPLE 8

Preparation of (2S,3S,4E)-2-Azidooctadec-1,3-O-di-(tert-butyl)-silanediyl-4-ene-1,3-diol (D-erythro-2-azido-sphingosine)

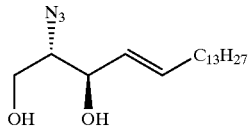

TBAF (1.0 mmol; 1.5 mL) was added to a cooled (273K) and stirred mixture of (2S,3S,4E)-2-Azidooctadec-1,3-O-di-(tert-butyl)silanediyl-4-ene-1,3-diol (0.314 g; 0.68 mmol) and acetic acid (0.084 mL, 2.2 equiv.) in THF (6 mL). After 1 h, TLC analysis showed complete conversion of starting material into a compound with $R_f$=0.00 (EtOAc/petroleum light ether, 95:5, v/v). The reaction was diluted with diethyl ether (50 mL), aqueous sodium acetate (2 M; 50 mL) was added. The organic layer was separated and washed with water, dried (MgSO$_4$) and concentrated under reduced pressure. The residue was purified by silica gel column chromatography. Elution was performed with DCM/MeOH (100:0→95:5, v/v) giving a of colourless oil. The purity was at least 95%.

$^1$H-NMR (CDCl$_3$): δ=0.88 (t, 3H, CH$_3$), 1.26 (s, 22H, 11×CH$_2$), 2.07 (m, 2H, CH$_2$), 2.21 (s, 2H, 2×OH), 3.50 (dd, 1H, H-2, $J_{1eq,2}$=$J_{2,3}$=5.1 Hz, $J_{1ax,2}$=11.0 Hz), 3.78 (d, 2H, H$_2$), 4.25 (t, 1H, H-3, $J_{2,3}$=5.9 Hz, $J_{3,4}$=6.6 Hz), 5.54 (dd, 1H, H-4, $J_{3,4}$=6.6 Hz, $J_{4,5}$=15.4 Hz), 5.82 (quin. 1H, H-5, $J_{5,6a}$=6.6 Hz, $J_{5,6b}$=6.5 Hz, $J_{4,5}$=15.4 Hz). $^{13}$C{$^1$H}-NMR (CDCl$_3$): δ=14.0 (CH$_3$), 22.6, 28.9, 29.6, 31.8, 32.2 (CH$_2$), 62.4 (C-1), 66.7 (C-2), 73.5 (C-3), 128.0 (C-5), 135.9 (C-4).

EXAMPLE 9

Preparation of (2S,3S,4R)-2-N-tert-Butoxycarbonyla-mino-1,3,4-octadecanetriol (4)

To a stirred suspension of phytosphingosine (3, 10.0 g: 31.5 mmol) in THF (250 mL) were added TEA (5.3 ml, 37.8 mmol) and di-tert-butyl dicarbonate (7.56 g; 33.0 mmol). After 30 min. TLC analysis indicated the complete conversion of starting material into a compound with $R_f$=0.40 (MeOH/DCM, 1:9, v:v) Evaporation of the solvent followed by dissolving the residue in hot ethyl acetate (250 mL) and cooling to 0° C. afforded white crystals. Yield 12.1 g (92%).

Mp 86° C. Optical rotation 7.9° (c=1.0, CHCl$_3$) $^1$H-NMR (CDCl$_3$): δ=0.88 (t, 3H, CH$_3$), 1.26 (s, H, CH$_2$), 1.38 (s, 9H, tBu Boc), 1.90 (m, 2H, CH$_2$), 2.17 (m, 2H, CH$_2$), 3.78 (m, 2H, H-2, H-4), 3.97 (dd, 1H, H-1a, $J_{1a,1b}$=8.8 Hz, $J_{1a,2}$=6.6 Hz), 4.06 (dd, 1H, H-3, J=5.1 Hz, J=7.3 Hz), 4.17 (dd, 1H, H-1b, $J_{1a,1b}$=8.8 Hz, $J_{1b,2}$=5.9 Hz). $^{13}$C{$^1$H}-NMR (CDCl$_3$): δ=14.0 (CH$_3$), 22.7, 26.0 (×CH$_2$), 28.4 (tBu Boc), 29.7 (×CH$_2$), 31.9, 32.8 (×CH$_2$), 52.7 (C-2), 61.7 (C-1), 72.9 (C-4), 75.8 (C-3), 80.0 (Cq Boc), 156.4 (C=O Boc). ES-MS: m/z 418.6 [M+H]$^+$, 440.4 [M+Na]$^+$, 835.9 [2M+H]$^+$, 858.0 [2M+Na]$^+$.

EXAMPLE 10

Preparation of (2S,3S,4R)-2-N-tert-Butoxycarbonyla-mino-1,3-O-di-(tert-butyl)silanediyl-1,3,4-octadecanetriol (5)

To a cooled (−40° C.) solution of 4 (5.00 g, 12.0 mmol) in DMF (60 mL) was added, over a period of 15 min, tBu$_2$Si(OTf) (4.33 mL, 12.6 mmol). The solution was stirred an additional 1 h, pyridine was added (2.03 mL, 25.1 mmol) and stirring was continued for an additional hour. The solution was diluted with diethyl ether (100 mL) and washed with aqueous NaHCO$_3$ (1×50 mL, 10%), water (3×50 mL), dried (MgSO$_4$) and concentrated. Flash column chromatography of the residue on silica gel with petroleum ether/EtOAc (100:0→90:10, v/v) gave 6.488 g (97%) of colorless oil.

Optical rotation 24.0° (c=1.0, CHCl$_3$) $^1$H-NMR (CDCl$_3$): δ=0.88 (t, 3H, CH$_3$), 1.01 (s, 9H, tBu), 1.04 (s, 9H, tBu), 1.26 (s, 14H, 12×CH$_2$), 1.43 (s, 9H, tBu), 1.52 (m, 2H, CH$_2$), 2.05 (s, 1H, OH), 3.66 (dd, 1H, H-3, $J_{2,3}$=9.5 Hz, $J_{3,4}$=4.4 Hz), 3.70 (dd, 1H, H-1ax, $J_{1ax,1eq}$=9.5 Hz, $J_{1,2}$=10.2 Hz), 3.85 (br. s, 1H, H-2), 3.93 (dd, 1H, H-1eq, $J_{1ax,1eq}$=9.5 Hz, $J_{1eq,2}$=2.9 Hz), (br. s, 1H, H-4), 3.93 (m, 1H, H-4, $J_{3,4}$=4.4 Hz, $J_{4,5}$=9.5 Hz), 4.37 (br. s, 1H, NH). $^{13}$C{$^1$H}-NMR (CDCl$_3$): δ=14.0 (CH$_3$), 20.2 (Cq tBu) 22.6, 25.6 (2×CH$_2$), 26.9, 27.4, 28.3 (3×tBu), 29.3, 29.6, 30.8, 31.8 (×CH$_2$), 49.6 (C-2), 67.4 (C-1), 72.7 (C-4), 79.7 (Cq tBu), 80.2 (C-3), 155.0 (C=O Boc). ES-MS: m/z 580.6 [M+Na]$^+$.

EXAMPLE 11

Preparation of (2S,3S)-2-N-tert-Butoxycarbonyla-mino-1,3-di-(tert-butyl)silanediyl-4-oxo-1,3-octadecanediol (6)

Acetic anhydride (2.4 mL) was added to a solution of 5 (0.599 g; 1.07 mmol) in anhydrous DMSO (4 mL). After stirring for 16 h, the reaction mixture was diluted with diethyl ether (50 mL), successively washed with aqueous NaHCO$_3$ (3×50 mL, 10%), water (1×50 mL), dried (MgSO$_4$), and concentrated. The crude product was purified by silica gel column chromatography. Elution was performed with petroleum ether/EtOAc (100:0→90:10, v/v) giving 0.591 g (99%) of colorless oil.

Optical rotation 4.1° (c=1.0, CHCl$_3$). $^1$H-NMR (CDCl$_3$): δ=0.88 (t, 3H, CH$_3$), 1.03 (s, 9H, tBu), 1.07 (s, 9H, tBu), 1.25 (br. s, 2H, CH$_2$), 1.39 (s, 9H, tBu Boc), 1.55 (m, 2H, CH$_2$), 2.73 (m, 2H, CH$_2$-5), 3.75 (t, 1H, H-1ax, $J_{1ax,1eq}$=9.5 Hz, $J_{1,2}$=10.2 Hz), 3.93 (m, 1H, H-2, $J_{1eq,2}$=4.4 Hz, $J_{1ax,2}$=10.2 Hz, $J_{2,3}$=9.5 Hz, $J_{2,NH}$=8.8 Hz), 4.13 (d, 1H, H-3, $J_{2,3}$=9.5 Hz), 4.14 (dd, 1H, H-1 eq, $J_{1ax,1eq}$=9.5 Hz, $J_{1eq,2}$=4.4 Hz), 4.43 (br. d, 1H, NH, $J_{2,NH}$=8.0 Hz). $^{13}$C{$^1$H}-NMR (CDCl$_3$): δ=14.0 (CH$_3$), 20.1 (Cq tBu) 22.6, 25.5 (×CH$_2$), 27.0, 27.3 28.1 (3×tBu), 29.1, 29.6, 30.9, 31.9 36.8 (×CH$_2$), 49.8 (C-2), 67.4 (C-1), 79.9 (Cq Boc), 82.8 (C-3), 154.9 (C=O Boc), 210.6 (C-4). ES-MS: m/z 578.7 [M+Na]$^+$.

EXAMPLE 12

Preparation of (2S,3S,4Z)-2-N-tert-Butoxycarbonyla-minooctadec-1,3-O-di-(tert-butyl)silan-ediyl-4enoltriflate-1,3-diol (7)

Over a period of 5 min, a solution of 6 (0.100 g; 0.18 mmol) in THF (1 mL) was added to a cooled (−78° C.) solution of potassium bis(trimethylsilyl)amide (KHMDS; 4.0 mmol, 8 mL, 0.5 M in toluene) in THF (2 mL). The mixture was stirred for an additional 1 h, after which, over a period of 10 min, a solution of N-phenyltrifluoromethane-sulfonimide (0.193 g; 0.54 mmol) in THF (5 mL) was added. After stirring for 1 h at −20° C., aqueous NaHCO$_3$ (10%, 2 mL) and diethyl ether (50 mL) were added. The organic layer was successively washed with aqueous NaHCO$_3$ (10%, 20 mL), dried (MgSO$_4$) and concentrated. The crude product was purified by silica gel column chromatography.

Elution was performed with petroleum ether/EtOAc/TEA (100:0:0.5→90:10:0.5, v/v) giving 0.108 g (89%) of colorless oil. $R_f$=0.42 (petroleum ether/EtOAc, 90:10, v/v).

Optical rotation 3.4° (c=1.0, CHCl$_3$). $^1$H-NMR (CDCl$_3$): δ=0.88 (t, 3H, CH$_3$), 1.01 (s, 9H, tBu), 1.03 (s, 9H, tBu), 1.25 (br. s, 2H, CH$_2$), 1.42 (s, 9H, tBu Boc), 2.20 (m, 2H, CH$_2$-6), 3.79 (t, 1H, H-1ax, $J_{1ax,1eq}$=9.5 Hz, $J_{1ax,2}$=10.2 Hz), 3.92 (m, 1H, H-2, $J_{1eq,2}$=3.7 Hz, $J_{1ax,2}$=10.2 Hz, $J_{2,3}$=9.5 Hz, $J_{2,NH}$=9.5 Hz), 4.08 (dd, 1H, H-1eq, $J_{1ax,1eq}$=9.5 Hz, $J_{1eq,2}$=3.7 Hz), 4.42 (t, 2H, H-3, NH, $J_{2,3}$=9.5 Hz, $J_{2,NH}$=9.5 Hz), 5.82 (t, 1H, H-5, J=7.3 Hz, J=4.6 Hz). $^{13}$C{$^1$H}-NMR (CDCl$_3$): δ=14.0 (CH$_3$), 19.9 (Cq tBu) 22.6, 25.5, 26.8 (×CH$_2$), 27.1, 28.1 28.3 (3×tBu), 29.3, 29.6, 31.9 (×CH$_2$), 50.8 (C-2), 66.9 (C-1), 76.2 (C-3), 80.0 (Cq Boc), 123.5 (C-5), 146.7 (C-4), 154.6 (C=O Boc). ES-MS: m/z 710.6 [M+Na]$^+$.

EXAMPLE 13

Preparation of (2S,3S,4E)-2-N-tert-Butoxycarbonyla-minooctadec-1,3-O-di-(tert-butyl)silan-ediyl-4ene-1,3-diol (8)

Formic acid (0.037 mL, 0.99 mmol) was added to a mixture of 7 (0.227; 0.33 mmol), bis(triphenylphosphine) palladium acetate (1% mol, 0.025 g) and TEA (0.183 mL, 1.32 mmol) in DMF (5 mL). The solutions were first deoxygenated using an ultrasonic bath for 1 hour. After stirring the mixture for 6 h at 60° C., the solvents were evaporated and the residue purified by silica gel column chromatography. Elution was performed with petroleum ether/EtOAc (100:0→90:10, v/v) giving 0.164 g (91%) of colorless oil. $R_f$=0.20 (petroleum ether/EtOAc, 90:10, v/v).

Optical rotation 23.40 (c=1.0, CHCl$_3$). $^1$H-NMR (CDCl$_3$): δ=0.88 (t, 3H, CH$_3$), 1.01 (s, 9H, tBu), 1.03 (s, 9H, tBu), 1.25 (br. s, H, ×CH$_2$), 1.41 (s, 9H, tBu Boc), 2.02 (m, 2H, CH$_2$-6), 3.69–4.17 (m, 5H, H2-1, H-2, H-3, NH), 5.48 (dd, 1H, H-4, $J_{4,5}$=15.4 Hz, $J_{3,4}$=6.6 Hz), 5.71 (quin., 1H, H-5, $J_{4,5}$=15.4 Hz, $J_{5,6a}$=$J_{5,6b}$6.6 Hz). $^{13}$C{$^1$H}-NMR (CDCl$_3$): δ=14.0 (CH$_3$), 20.0 (Cq tBu) 22.6, (CH$_2$), 27.1, 27.4 28.3 (3×tBu), 29.1, 29.3, 29.6, 31.9, 32.2 (×CH$_2$), 52.2 (C-2), 67.2 (C-1), 79.0 (C-3), 79.6.0 (Cq Boc), 129.5 (C-5), 133.8 (C-4), 155.0 (C=O Boc). ES-MS: m/z 540.6 [M+H]$^+$, 562.3 [M+Na]$^+$, 578.8 [M+K]$^+$.

EXAMPLE 14

Preparation of (2S,3S,4E)-2-N-tert-Butoxycarbonyla-minooctadec-4-ene-1,3-diol (9)

Acetic acid (0.034 mL, 0.72 mmol) and TBAF (0.66 mmol; 0.66 mL) were added to a cooled (0° C.) solution of 8 (0.164 g; 0.30 mmol) in THF (5 mL). After 2 h, TLC analysis showed complete conversion of starting material into a compound with $R_f$=0.57 (DCM/MeOH, 90:10, v/v). The reaction was diluted with diethyl ether (50 mL) and successively washed with aqueous sodium acetate (2 M; 50 mL), water (50 mL), dried (MgSO$_4$) and concentrated. The residue was purified by silica gel column chromatography. Elution was performed with DCM/MeOH (100:0→95:5, v/v) giving 0.129 g (quantitative) of colorless oil.

Optical rotation 2.00 (c=2.58, CHCl$_3$). $^1$H-NMR (CDCl$_3$): δ=0.88 (t, 3H, CH$_3$), 1.25 (br. s, H, ×CH$_2$), 1.45 (s, 9H, tBu Boc), 2.05 (q, 2H, CH$_2$-6), 2.42 (br. s, 2H, OH), 3.59 (br. s, 1H, H-2), 3.70 (dd, 1H, H-1a, $J_{1a,1b}$=11.0 Hz, $J_{1a,2}$=3.7 Hz), 3.93 (dd, 1H, H-1b, $J_{1a,1b}$=11.0 Hz, $J_{1ax,2}$=3.7 Hz), 4.32 (t, 1H, H-3, J=5.1), 5.29 (br. s, 1H, NH), 5.52 (dd, 1H, H-4, $J_{4,5}$=15.4 Hz, $J_{3,4}$=5.9 Hz), 5.72 (quin., 1H, H-5, $J_{4,5}$=15.4 Hz, $J_{5,6a}$=$J_{5,6b}$=6.6 Hz). $^{13}$C{$^1$H}-NMR (CDCl$_3$): δ=14.0 (CH$_3$), 22.6, (CH$_2$), 28.3 (Bu), 29.1, 29.3, 29.6, 31.9, 32.3 (×CH$_2$), 55.5 (C-2), 62.3 (C-1), 74.2 (C-3), 79.7 (Cq Boc), 128.9 (C-5), 133.9 (C-4), 156.2 (C=O Boc). ES-MS: m/z 400.3 [M+H]$^+$, 422.3 [M+Na]$^+$, 438.3 [M+K]$^+$, 799.6 [2M+H]$^+$, 821.8 [2M+Na]$^+$, 837.8. [2M+K]$^+$.

EXAMPLE 15

Preparation of (2S,3S,4E)-2-Aminooctadec-4-ene-1,3-diol (Sphingosine, 1)

At 0° C. trifluoroacetic acid (5 mL) was added to a solution of 9 (0.514 g; 1.28 mmol) in DCM (5 mL). After 1 h, TLC analysis showed complete conversion of starting material into baseline product (DCM/MeOH, 9:1, v/v). The reaction mixture was concentrated and co evaporated with toluene (3×5 mL). The residue was purified by silica gel column chromatography. Elution was performed with EtOAc/MeOH/H$_2$O (90:10:0→65:30:5, v/v) giving 0.400 g (87%) white crystalline fluffy.

mp: 70° C. Optical rotation −1.2° (c=1.74, CHCl$_3$). $^1$H-NMR (CDCl$_3$): δ=0.88 (t, 3H, CH$_3$), 1.26 (br. s, H, CH$_2$), 2.05 (q, 2H, CH$_2$-6), 2.28 (br. s, 3H, OH/NH$_2$/H$_2$O), 2.86 (br. s, 1 h, H-2), 3.66 (br. s, 2H, H$_2$-1), 4.05 (br. s, 1H, H-3), 5.46, (dd, 1H, H-4, $J_{4,5}$=15.4 Hz, $J_{3,4}$=6.6 Hz), 5.73 (quin., 1H, H-5, $J_{4,5}$=15.4 Hz, $J_{5,6a}$=$J_{5,6b}$=6.6 Hz). $^{13}$C{$^1$H}-NMR (CDCl$_3$): δ=14.0 (CH$_3$), 22.6, 29.3, 29.6, 31.8, 32.3 (CH$_2$), 56.2 (C-2), 63.1 (C-1), 74.5 (C-3), 129.1 (C-5), 134.4 (C-4). ES-MS: m/z 300.5 [M+H]$^+$.

EXAMPLE 16

Preparation of (2S,3S,4R)-2-N-Benzoylamino-1,3,4-octadecanetriol

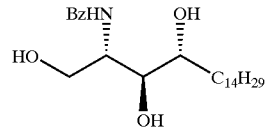

To a stirred suspension of phytosphingosine (10.0 g, 31.5 mmol) in THF (250 mL) containing TEA (5.27 ml, 37.8 mmol) was added benzoylchloride (3.84 mL, 33.1 mmol) and stirred for 30 min. The solvent was evaporated and the residue dissolved in hot ethyl acetate (250 mL), washed with aqueous HCl (1N, 2×50 mL), after cooling the organic layer to 0° C. white crystals were obtained. Yield 13.1 g (99%).

TLC (silica gel, diethylether/ethanol/ammoniumhydroxide, 6:3:1): $R_f$=0.75. mp 114° C. ES-MS: m/z 422.3 [M+H]$^+$, 444.6 [M+Na]$^+$, 865.9 [2M+Na]$^+$.

Optical rotation 13.60 (c=1.07 CHCl$_3$/MeOH, 5:1, v/v). $^1$H-NMR (CD$_3$OD/CDCl$_3$): δ=0.88 (t, 3H, CH$_3$), 1.28 (s, 24H, 12×CH$_2$), 1.49 (br. s, 2H, CH$_2$), 3.63 (m, 1H, H-4), 3.70 (m, 1H, H-3), 3.89 (m, 2H, H$_2$-1), 4.34 (m, 1H, H-2), 4.49 (s, 3H, 3×OH), 7.41–7.90 (m, 5H, CH-arom benzoyl). $^{13}$C{$^1$H}-NMR (CDCl$_3$): δ=13.4 (CH$_3$), 22.2, 25.3, 28.9, 29.2, 31.5, 32.6 (×CH$_2$), 52.2 (C-2), 60.7 (C-1), 72.1, 75.1 (C-3/C-4), 126.7, 128.1, 131.3 (CH-arom benzoyl), 133.1 (Cq benzoyl), 168.3 (C=O benzoyl).

EXAMPLE 17

Preparation of (2S,3S,4R)-2-N-Benzoylamino-1-O-trityl-1,3,4-octadecanetriol

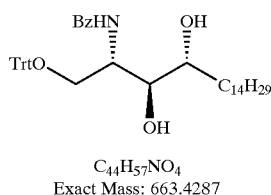

C₄₄H₅₇NO₄
Exact Mass: 663.4287

To a stirred suspension of (2S,3S,4R)-2-N-benzoylamino-1,3,4-octadecanetriol (58.9 g, 140 mmol) in EtOAc (600 mL) containing TEA (23 ml, 138 mmol), maintained at 80° C. was dropwise added a solution of triphenylmethyl chloride (42.9 g, 138 mmol) in EtOAc (200 mL). The mixture was stirred at 80° C. for 2.5 h. The solvent was washed successively with aqueous HCl (1N, 3×200 mL), aqueous NaHCO₃ (10%, 1×200 mL) and concentrated. Column chromatography of the residue over silica gel with toluene/EtOAc (1:0→3:2, v/v) gave title compound (92.8 g, 99%) as a colorless oil. $R_f$=0.80 (MeOH/EtOAc, 1:9).

ES-MS: m/z 686.7 [M+Na]⁺. Optical rotation 11.20 (c=1.04 CHCl₃). ¹H-NMR (CD₃OD/CDCl₃): δ=0.87 (t, 3H, CH₃), 1.25 (s, 24H, 12×CH₂), 1.44 (m, 2H, CH₂), 2.57 (br. t, 1H, OH-3), 3.35 (dd, 1H, H-3, $J_{2,3}$=8.0 Hz, $J_{3,4}$=8.4 Hz), 3.47 (dd, 2H, H-1a, OH-4, $J_{1a,1b}$=9.9 Hz, $J_{1a,2}$=4.4 Hz), 3.60 (dd, 1H, H-1b, $J_{1a,1b}$=9.9 Hz, $J_{1a,2}$=3.3 Hz), 3.69 (m, 1H, H-4), 4.47 (m, 1H, H-2, $J_{2,NH}$=$J_{2,3}$=8.0 Hz, $J_{1a,2}$=4.4 Hz, $J_{1b,2}$=3.3 Hz), 6.90 (d, 1H, NH, $J_{2,NH}$=8.0 Hz), 7.16–7.75 (m, 20H, CH-arom benzoyl/Trt). ¹³C{¹H}-NMR (CDCl₃): δ=14.0 (CH₃), 22.5, 25.6, 29.2, 29.5, 31.7 (×CH₂), 50.9 (C-2), 62.9 (C-1), 72.8, 75.5 (C-3/C-4), 87.3 (Cq Trt), 126.9–131.4 (CH-arom benzoyl/Trt), 134.0 (Cq benzoyl), 143.1 (Cq Trtarom), 167.2 (C=O benzoyl).

EXAMPLE 18

Preparation of (2S,3S,4R)-2-N-Benzoylamino-3,4-O-dibenzoyl-1-O-trityl-1,3,4-octadecanetriol

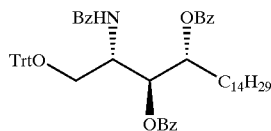

To a stirred solution of (2S,3S,4R)-2-N-benzoylamino-1-O-trityl-1,3,4-octadecanetriol (17.5 g, 26 mmol) in EtOAc (50 mL) containing TEA (8.0 mL, 57 mmol) was dropwise added benzoyl chloride (6.6 mL, 57 mmol) and stirred overnight. Excess of benzoyl chloride was quenched by the addition MeOH (5 mL). The mixture was diluted with EtOAc (50 mL) and successively washed with aqueous HCl (1N, 3×100 mL), aqueous NaHCO₃ (10%, 2×50 mL), dried (MgSO₄), and concentrated. Column chromatography of the residue over silica gel with petroleum ether/EtOAc (95:5→80:20, v/v) gave title compound (24.0 g, 100%) as a colorless oil. $R_f$=0.90 (petroleum ether/EtOAc, 2:1).

EXAMPLE 19

Preparation of (2S,3S,4R)-2-N-Benzoylamino-3,4-O-dibenzoyl-1,3,4-octadecanetriol

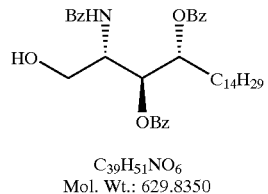

C₃₉H₅₁NO₆
Mol. Wt.: 629.8350

To a solution of (2S,3S,4R)-2-N-benzoylamino-3,4-O-dibenzoyl-1-O-trityl-1,3,4-octadecanetriol (52.4 g, 60.2 mmol) in MeOH/toluene (400 mL, 1:1, v/v) was added BF₃.O(Et)₂ (11.3 mL, 90.3 mmol) and the mixture was stirred for 1.5 h. The mixture was diluted with EtOAc (100 mL) and washed with aqueous NaHCO₃ (10%, 3×100 mL), dried (MgSO₄) and concentrated. Column chromatography of the residue over silica gel with petroleum ether/EtOAc (95:5→33:66, v/v) gave title compound (94 g, 99%) as a yellow oil. TLC (silica gel, petroleum ether/EtOAc, 2:1): $R_f$=0.40.

Optical rotation 50.60 (c=1.14 CHCl₃). ES-MS: m/z 630.5 [M+H]⁺, 652.4 [M+Na]⁺. ¹H-NMR (CDCl₃): δ=0.87 (t, 3H, CH₃), 1.21 (s, 24H, 12×CH₂), 2.06 (br. s, 2H, CH₂), 3.00 (t, 1H, OH), 3.75 (m, 2H, CH₂-1), 4.60 (m, 1H, H-2), 5.47 (m, 1H, H-4), 5.60 (dd, 1H, H-3), 7.21 (d, 1H, NH), 7.33–8.08 (m, 15H, CH-arom benzoyl). ¹³C{¹H}-NMR (CDCl₃): δ=14.0 (CH₃), 22.6, 25.6, 28.3, 29.5, 31.8, (×CH₂), 50.7 (C-2), 61.3 (C-1), 73.1, 74.0 (C-3/C-4), 127.1–133.9 (CH-arom benzoyl), 166.5, 167.5, (C=O benzoyl).

EXAMPLE 20

Preparation of 1-[4-(S)-(2-Phenyl-4.5-dihydro-oxazol-4-yl)]-(1S,2R)-hexadecane-1,2-O-dibenzoyl

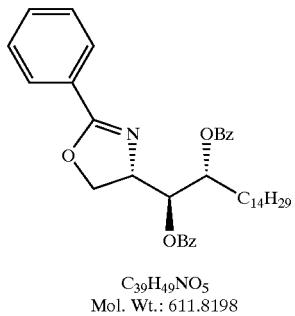

C₃₉H₄₉NO₅
Mol. Wt.: 611.8198

To solution of (2S,3S,4R)-2-N-benzoylamino-3,4-O-dibenzoyl-1,3,4-octadecanetriol (32.0 g, 50.8 mmol) in DCM (250 mL) containing TEA (75 mL, 531 mmol), maintained at 0° C. was added methanesulfonyl chloride (8.22 mL, 106.2 mmol). After 1 h, the reaction mixture was allowed to raise to ambient temperature and stirred for 18 h. The reaction was washed with aqueous HCl (1N. 3×200 mL), aqueous NaHCO₃ (10%, 200 mL), dried (MgSO₄) and concentrated. The residue was purified by silica gel column chromatography. Elution was performed with petroleum ether/EtOAc (95:5→85:15, v/v) giving 26.7 g (86%) of colorless oil. $R_f$=0.80 (petroleum ether/EtOAc, 3:1, v/v).

Optical rotation −50.0° (c=1.42 CHCl₃). ES-MS: m/z612.5 [M+H]⁺, 634.7 [M+Na]⁺. ¹H-NMR (CDCl₃): δ=0.88 (t, 3H, CH₃), 1.24 (s, 24H, 12×CH₂), 1.91 (dd, 2H, CH$_2$), 4.53 (dd, 1H, H-1, J$_{1,1'}$=8.8 Hz, J$_{1,2}$=10.2 Hz), 4.62 (dd, 1H, H-1, J$_{1,1'}$=8.4 Hz, J$_{1,2}$=6.9 Hz), 4.77 (ddd, 1H, H-2, J$_{1,2}$=10.2 Hz, J$_{1,2}$=6.6 Hz, J$_{2,3}$=3.7 Hz), 5.62 (m, 2H, H-3, H-3), 7.26–8.04 (m, 15H, CH-arom benzoyl, phenyloxazol). $^{13}$C{$^1$H}-NMR (CDCl$_3$): δ=14.0 (CH$_3$), 22.6, 25.3, 29.3, 29.6, 30.6, 31.8 (×CH$_2$), 66.6 (C-2), 69.1 (C-1), 73.4, 75.4 (C-3/C-4), 127.2–133.1 (CH-arom benzoyl, phenyloxazol), 165.3, 165.5, 165.7, (C=N, C=O benzoyl, phenyloxazol).

EXAMPLE 21

Preparation of 1-[4-(S)-(2-Phenyl-4,5-dihydro-oxazol-4-yl)]-(1S,2R)-hexadecane-1,2-diol

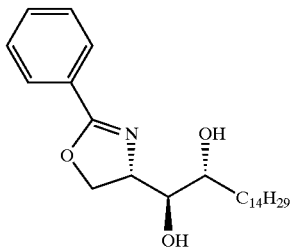

Potassium carbonate (15.0 g, 108 mmol) was added to a mixture of 1-[4-(S)-(2-phenyl-4,5-dihydro-oxazol-4-yl)]-(1S,2R)-hexadecane-1,2-O-dibenzoyl (13.4 g, 21.8 mmol) in chloroform/MeOH (100 mL, 3:1, v/v) and stirred for 18 h at 60° C. TLC analysis indicated the complete conversion of starting material into a compound with R$_f$=0.60 (DCM/MeOH, 9:1, v/v). After evaporating the solvents, the residue was dissolved in hot EtOAc (500 mL) washed with water (3×100 mL) and the organic layer concentrated. The crystals were crystallized from hot petane yielding 8.8 g of white crystals (100%).

mp 137–138° C. Optical rotation 24.8° (c=1.60 CHCl$_3$/methanol, 5:1, v/v). ES-MS: m/z404.3 [M+H]$^+$, 426.1 [M+Na]$^+$, 444.5 [M+K]$^+$, 807.6 [2M+H]$^+$, 829.5 [2M+Na]$^+$, 847.9 [2M+K]$^+$. $^1$H-NMR (CDCl$_3$): δ=0.88 (t, 3H, CH$_3$), 1.25 (s, 24H, 12×CH$_2$), 1.52 (m, 2H, CH$_2$), 2.17 (d, 1H, OH), 3.27 (d, 1H, OH), 3.71 (m, 1H, H-3), 3.81 (m, 1H, H-4), 4.40–4.61 (m, 3H, H$_2$-1, H-2), 7.26–7.92 (m, 5H, CH-arom phenyloxazol). $^{13}$C{$^1$H}-NMR (CDCl$_3$): δ=13.9 (CH$_3$), 22.5, 25.4, 29.1, 29.5, 31.7, 32.9 (×CH$_2$), 68.4 (C-2), 69.3 (C-1), 73.5, 74.9 (C-3/C-4), 126.9–132.9 (CH-arom phenyloxazol), 165.4 (C=N phenyloxazol).

EXAMPLE 22

Preparation of 1-[4-(S)-(2-Phenyl-4,5-dihydro-oxazol-4-yl)]-(1S,2R)-1-hydroxy-2-O-mesyl-hexadecane

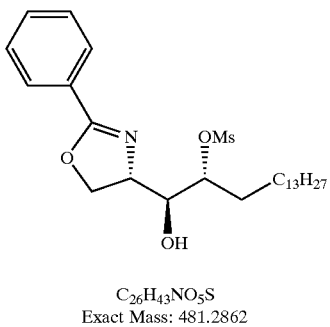

C$_{26}$H$_{43}$NO$_5$S
Exact Mass: 481.2862

To a solution of 1-[4-(S)-(2-phenyl-4,5-dihydro-oxazol-4-yl)]-(1S,2R)-hexadecane-1,2-diol (1.148 g, 2.84 mmol) in chloroform/pyridine (20 mL, 1:1, v/v) was added methane sulfonyl chloride (0.231 mL, 2.98 mmol) and stirred for 8 h. Methanol (0.5 mL) was added and the solvent was evaporated in vacuo. The residue was taken up in EtOAc (50 mL) and washed successively with aqueous HCl (1N, 3×50 mL), aqueous NaHCO$_3$ (10%, 50 mL), brine (50 mL), dried (MgSO$_4$) and concentrated. Column chromatography if the residue over silica gel with petroleum ether/EtOAc (9:1→7:3, v/v) gave title coumpound (0.917 g, 67%) as a colorless oil. TLC (silica gel, petroleum ether/EtOAc, 2:1): R$_f$=0.50.

$^1$H-NMR (CDCl$_3$): δ=0.88 (t, 3H, CH$_3$), 1.26 (s, 24H, 12×CH$_2$), 1.82 (m, 2H, CH$_2$), 3.12 (s, 3H, Ms), 4.19 (d, 1H, H-3), 4.47 (m, 3H, H$_2$-1, H-2), 4.86 (dt, 1H, H-4), 7.27–7.74 (m, 5H, CH-arom phenyloxazol). $^{13}$C{$^1$H}-NMR (CDCl$_3$): δ=14.0 (CH$_3$), 22.5, 24.9, 29.5, 31.3, 31.7, (×CH$_2$), 38.3 (CH$_3$ Ms), 67.1 (C-2), 67.7 (C-1), 71.6, (C-3), 84.2 (C-4), 126.4 (Cq phenyloxazol), 128.0, 128.1, 131.4 (CH-arom phenyloxazol), 165.7 (C=N phenyloxazol).

EXAMPLE 23

Preparation of 1-[4-(S)-(2-Phenyl-(4.5-dihydro-oxazol)-4-yl]-(1S,2R)-1,2-oxiranyl-hexadecane

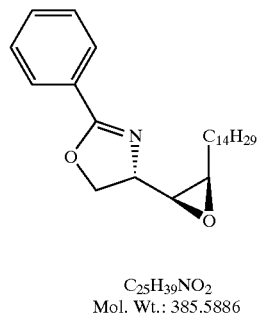

C$_{25}$H$_{39}$NO$_2$
Mol. Wt.: 385.5886

To a solution of 1-[4-(S)-(2-Phenyl-4,5-dihydro-oxazol-4-yl)]-(1S,2R)-1-hydroxy-2-O-mesyl-hexadecane (0.208 g, 0.43 mmol) in THF (4 mL), maintained at 0° C., was added potassium tert-butylate (0.048 g, 0.43 mmol), and the mixture was stirred for 2 h. The mixture was diluted with EtOAc (50 mL) and successively washed with water (2×20 mL), brine (20 mL), dried (MgSO$_4$) and concentrated. Column chromatography of the residue over silica gel with petroleum ether/EtOAc EtOAc (x:x→x:x, v/v) gave title compound (0.166 g, 99%) as a crystalline solid. TLC (silica gel, petroleum ether/EtOAc, 1:1): R$_f$=0.70.

Optical rotation 24.8° (c=1.60 CHCl$_3$/MeOH 5:1, v/v). ES-MS: m/z 386.3 [M+H]$^+$, 408.2 [M+Na]$^+$. $^1$H-NMR (CDCl$_3$): δ=0.88 (t, 3H, CH$_3$), 1.25 (s, 24H, 12×CH$_2$), 1.55 (m, 2H, CH$_2$), 2.95 (dd, 1H, H-4), 3.05 (dt, 1H, H-3), 4.27 (m, 1H, H-2), 4.41–4.56 (m, 2H, H$_2$-1), 7.35–7.97 (m, 5H, CH-arom phenyloxazol). $^{13}$C{$^1$H}-NMR (CDCl$_3$): δ=14.0 (CH$_3$), 22.7, 25.9, 29.4, 29.6, 31.6, 33.4 (×CH$_2$), 55.8, 59.1 (C-3/C-4), 66.4 (C-2), 68.9 (C-1), 128.3–131.5 (CH-arom phenyloxazol), 165.2 (C=N phenyloxazol).

EXAMPLE 24

Preparation of 1-[4-(S)-(2-Phenyl-4,5-dihydro-oxazol)-4-yl]-(1S,2R)-2-iodo-1-trimethylsilanyloxyhexadecane

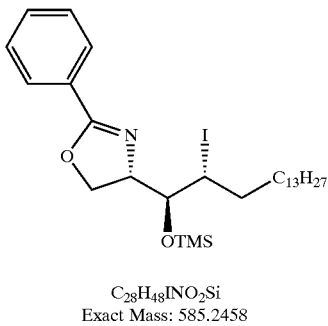

$C_{28}H_{48}INO_2Si$
Exact Mass: 585.2458

To a solution of 1-[4-(S)-(2-Phenyl-(4,5-dihydro-oxazol)-4-yl]-(1S,2R)-1,2-oxiranyl-hexadecane (0.157 g, 0.41 mmol) in acetornitrile (4 mL), maintained at 40° C., were added DBN (0.097 mL, 0.82 mmol) and TMSI (0.061 mL, 0.45 mmol) and the mixture was stirred for 3 h. The solvent was evaporated and the residue taken up in EtOAc (50 mL) and washed successively with aqueous HCl (1N, 2×50 mL), aqueous NaHCO$_3$ (10%, 50 mL), brine (50 mL), dried (MgSO$_4$) and concentrated. Column chromatography of the residue over silica gel with petroleum ether/EtOAc (10:0→9:1, v/v) gave title compound (0.14 g, 59%) as a crystalline solid. TLC (silica gel, petroleum ether/EtOAc, 1:1): R$_f$=0.90.

ES-MS: m/z 386.3 [M+H]$^+$, 408.2 [M+Na]$^+$. $^1$H-NMR (CDCl$_3$): δ=0.08 (s, 9H, TMS), 0.88 (t, 3H, CH$_3$), 1.26 (s, 22H, 11×CH$_2$), 1.63 (m, 2H, CH$_2$), 1.82 (m, 2H, CH$_2$), 4.01–4.15 (m, 2H, H-3, H-4), 4.35–4.49 (m, 2H, H$_2$-1), 4.80 (ddd, 1H, H-2), 7.36–7.96 (m, 5H, CH-arom phenyloxazol). $^{13}$C{$^1$H}-NMR (CDCl$_3$): δ=0.6 (CH$_3$ TMS), 14.1 (CH$_3$), 22.7, 28.8, 29.6, 31.9, 35.4 (×CH$_2$), 41.0 (C-4), 68.0 (C-1), 70.6 (C-2), 78.2 (C-3), 127.7 (Cq phenyloxazol), 128.2, 128.3, 131.3 (CH-arom phenyloxazol), 164.3 (C=N phenyloxazol).

EXAMPLE 25

Preparation of 1-[4-(S)-(2-Phenyl-4,5-dihydro-oxazol)-4-yl]-(1S,2E)-1-trimethylsilanyloxyhexadec-2-enyl

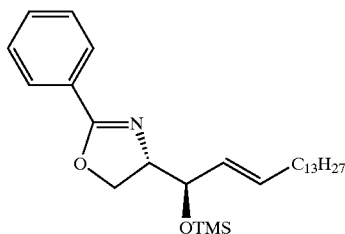

To a solution of 1-[4-(S)-(2-Phenyl-(4,5-dihydro-oxazol)-4-yl]-(1S,2R)-1,2-oxiranyl-hexadecane ((0.456, 1.18 mmol) in acetonitrile (10 mL), maintained at 40° C. was added TMSI (0.177 mL, 1.30 mmol) and the mixture was stirred for 20 min at 40° C. DBN (0.465 mL, 3.89 mmol) was added and the mixture was refluxed for 1.5 h. Subsequenlty, the solvent was concentrated and column chromatografy of the residue using petroleum ether/EtOAc (1:0→4:1) gave title compound (0.375, 69%) as a colorless oil. TLC (silica gel, petroleum ether/EtOAc, 4:1): R$_f$=0.90.

Optical rotation 6.2° (c=1.28 CHCl$_3$). ES-MS: m/z 458.4 [M+H]$^+$, 480.4 [M+Na]$^+$. $^1$H-NMR (CDCl$_3$): δ=0.04 (s, 9H, TMS), 0.87 (t, 3H, CH$_3$), 1.26 (s, 22H, 11×CH$_2$), 1.37 (br. t, 2H, CH$_2$), 2.05 (dd, 2H, CH$_2$), 4.27 (dd, H-1a), 4.28 (m, 1H, H-2), 4.39 (m, 1H, H-3), 4.42 (dd, 1H, H-1b), 5.45 (ddt, 1H, H-4, J$_{4,5}$=15.2 Hz, J$_{3,4}$=6.6 Hz), 5.71 (ddt, 1H, H-5, J$_{4,5}$=15.2 Hz, J$_{5,6=6.9}$ Hz), 7.37–7.95 (m, 5H, CH-arom phenyloxazol). $^{13}$C{$^1$H}-NMR (CDCl$_3$): δ=0.3 (CH$_3$ TMS), 14.1 (CH$_3$), 22.6, 29.1, 29.2, 29.3, 29.4, 29.6, 31.9, 32.2 (×CH$_2$), 67.9 (C-1), 71.7 (C-2), 73.8 (C-3), 127.9 (Cq phenyloxazol), 128.2, 131.1 (CH-arom phenyloxazol), 129.9 (C-4), 132.1 (C-5), 164.4 (C=N phenyloxazol).

EXAMPLE 26

Preparation of (2S,3S,4E)-2-Amino-octadec-4-ene-1,3-diol(D-erythro-sphingosine)

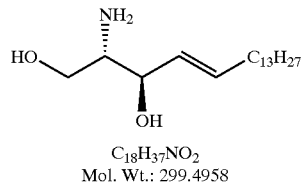

$C_{18}H_{37}NO_2$
Mol. Wt.: 299.4958

To a solution of 1-[4-(S)-(2-Phenyl-4,5-dihydro-oxazol)-4-yl]-(1S,2E)-1-trimethylsilanyloxyhexadec-2-enyl (0.133, 0.29 mmol) in THF (5 mL) was added aqueous HCl (2 N, 4.8 mL), and stirred for 18 h. The mixture was diluted with chloroform/MeOH (20 mL, 87:13 v/v) and water (10 mL). The organic phase was separated and the aqueous phase extracted with a chloroform/methanol mixture (2×20 mL, 87:13 v/v). The combined organic layers were dried (MgSO$_4$) and concentrated. The residue was dissolved in MeOH (5 mL) and aqueous NaOH (50 eq), was added and the mixture refluxed for 2 h. The cooled reaction mixture was diluted with water (10 mL) and extracted with diethyl ether (3×20 mL). The organic layer was dried (MgSO$_4$) and concentrated. Column chromatography of the residue over silica gel with EtOAc/MeOH/NH$_4$OH (90:10:0→40:10:1) gave title compound (0.073 g, 85%) as a white solid. TLC (silica gel, diethyl ether/EtOH/NH$_4$OH, 6:3:1): R$_f$=0.50.

Optical rotation 1.4° (c=0.42 CHCl$_3$). ES-MS: m/z 300.4 [M+H]$^+$, 322.4 [M+Na]$^+$. $^1$H-NMR (CDCl$_3$): δ=0.87 (t, 3H, CH$_3$), 1.24 (s, 22H, 11×CH$_2$), 2.03 (q, 2H, CH$_2$), 2.87 (br. s, 5H, H-2, NH$_2$, 2×OH), 3.65 (br. s, 2H, H$_2$-1), 4.06 (br. s, 1H, H-3), 5.44 (dd, 1H, H-4, J$_{4,5}$=15.4 Hz, J$_{3,4}$=5.9 Hz), 5.71 (dt, 1H, H-5, J$_{4,5}$=15.4 Hz, J$_{5,6}$=6.6 Hz).

Hertweck, C.; Šebek, P.; Svatoš

EXAMPLE 27

Preparation of (2S,3S,4E)-2-Acetamido-1,3-diacetyl-octadec-4-ene-1,3-diol

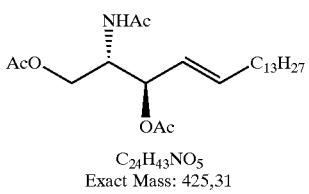

C$_{24}$H$_{43}$NO$_5$
Exact Mass: 425,31

To a solution of 1-[4-(S)-(2-Phenyl-4,5-dihydro-oxazol)-4-yl]-(1S,2E)-1-trimethylsilanyloxyhexadec-2-enyl (0.322, 0.70 mmol) in THF (x mL) was added aqueous HCl (2 N, x.x mL), and stirred for 18 h. The mixture was diluted with chloroform/MeOH (20 mL, 87:13 v/v) and water (10 mL). The organic phase was separated and the aqueous phase extracted with a chloroform/methanol mixture (2×20 mL, 87:13 v/v). The combined organic layers were dried (MgSO$_4$) and concentrated. The residue was dissolved in MeOH (xx mL) and aqueous NaOH (50 eq) and refluxed for 2 h. The cooled mixture was diluted with water (10 mL) and extracted with diethyl ether (3×20 mL). The organic layer was dried (MgSO$_4$) and concentrated. The residue was dissolved in pyridine (2 mL) and acetic anhydride (2 mL) was added, and the mixture was stirred for 4 h. The mixture was concentrated. Column chromatography of the residue over silica gel with petroleum ether/EtOAc (50:50→0:100) gave title compound (0.240 g, 80%) as a white solid. TLC (silica gel, petroleum ether/EtOAc, 1:1): R$_f$=0.20.

Optical rotation −13.2° (c=1.00 CHCl$_3$). $^1$H-NMR (CDCl$_3$): δ=$^{13}$C{$^1$H}-NMR (CDCl$_3$): δ=

While the present invention has been described and shown with respect to preferred embodiments thereof, it will be understood by those skilled in the art that the foregoing and other changes in form and detail may be made without departing from the spirit and scope of the present application. It is therefore intended that the present application not be limited to the exact forms described and illustrated, but fall within the scope of the appended claims.

What is claimed is:

1. A method for the production of a sphingoid base according to formula

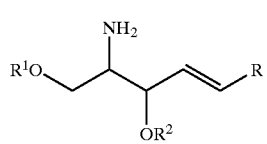
(formula II)

in which
R is a hydrocarbon chain having 5–50 carbon atoms, which may be a straight chain or branched, saturated or contain one or more double bonds, and which may contain one or more functional groups, and R$^1$ and R$^2$ may be the same or different and may be H or a hydrocarbon chain having 1–10 carbon atoms, which may be a straight chain or branched, saturated or contain one or more double bonds, and which may contain one or more functional groups, the method comprising the steps of
dissolving a starting compound according to formula III or a salt thereof in a substantially inert solvent,

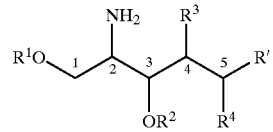
(formula III)

in which R$^1$, R$^2$, are as defined above
R$^3$ and R$^4$ may be the same or different and may be H, OH, or a hydrocarbon chain having 1–10 carbon atoms, which may be a straight chain or branched, saturated or contain one or more double bonds, and which may contain one or more functional groups,
and R' is a hydrocarbon chain having 3–48 carbon atoms, which may be a straight chain or branched, saturated or contain one or more double bonds, and which may contain one or more functional groups, the functional groups being selected from a hydroxyl group, an alkoxy group, a primary, secondary or tertiary amine, a thiol group, a thioether or a phosphorous containing functional group, protecting the NH$_2$ group of the starting compound of formula (III) with a NH$_2$ protecting group,
performing an elimination reaction to form a double bond between the C-4 and C-5 carbon atoms of the starting compound of the formula (III), and
removing the NH$_2$ protecting group.

2. A method for the production of a sphingoid base according to the formula

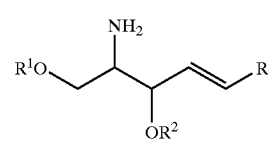
(formula II)

in which
R is a hydrocarbon chain having 5–50 carbon atoms, which may be a straight chain or branched, saturated or contain one or more double bonds, and which may contain one or more functional groups, and
R$^1$ and R$^2$ may be the same or different and may be H or a hydrocarbon chain having 1–10 carbon atoms, which may be a straight chain or branched, saturated or contain one or more double bonds, and which may contain one or more functional groups,
the method comprising the steps of
dissolving a starting compound according to formula IV or a salt thereof in a substantially inert solvent,

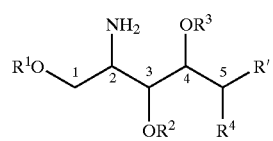
(formula IV)

in which R$^1$ and R$^2$ are as defined above,
R$^3$ is an alkyl group, an allyl, an ester, a sulfoxide, a sulphonyl group, a halogen, a sulfoxide group, a S-peroxide group, a Se—R group, a CH—Se—R, or a CH—SeO—R group,
R' is a hydrocarbon chain having 3–48 carbon atoms, which may be straight chain or branched, saturated or contain one or more double bonds, and which may contain one or more functional groups, and R⁴ is H, OH, or a hydrocarbon chain having 1–10 carbon atoms, which may be a straight chain or branched, saturated or contain one or more double bonds, and which may contain one or more functional groups, protecting the NH₂ group of the starting compound of formula (IV) with a NH₂ protecting group, performing an elimination reaction to form a double bond between the C-4 and C-5 carbon atoms of the starting compound of formula (IV), and removing the NH₂ protecting group.

3. The method of claim 1 wherein the compound of formula III is a compound corresponding to formula V:

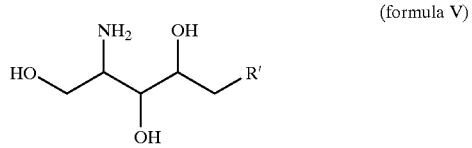

(formula V)

in which R' is as defined above.

4. The method of claim 3 wherein the starting compound is a sphinganine, phytosphingosine, monoacetylphytosphingosine, tetraacetylphytosphingosine or a derivative or a salt thereof.

5. The method of claim 3 wherein the starting compound is a phytosphingosine sphinganine, or a derivative or a salt thereof, the method comprising the steps of protecting the NH₂ group of the compound of formula (V) with a NH₂ protecting group, protecting the C-1 OH group of the compound of formula (V) with a protecting group selective to the C-1 OH group, protecting the C-3 OH group of the compound of formula (V) with a protecting group selective to the C-3 OH group, performing an elimination reaction to form a double bond between the C-4 and C-5 carbon atoms of the compound of formula (V), and removing the OH protecting groups and the NH₂ protecting group.

6. The method of claim 3 wherein the starting compound is a phytosphingosine or a salt thereof, and the method comprises the steps of protecting the NH₂ group of the compound of formula (V) with a NH₂ protecting group, protecting the C-1 OH group of the compound of formula (V) with a protecting group selective to the C-1 OH group, protecting the C-3 OH group of the compound of formula (V) with a protecting group selective to the C-3 OH group, performing an elimination reaction to form a double bond between the C-4 and C-5 carbon atoms of the compound of formula (V), removing the OH protecting groups, and removing the NH₂ protecting group.

7. The method of claim 6, wherein the C-4 OH of the compound of formula (V) is coupled to an electron withdrawing group which activates the C-4 OH group prior to said elimination reaction.

8. The method of claim 1 wherein the NH₂ group is protected as an amide, an cyclic amine, an imine, an azide, an oxazoline or a carbamate group.

9. The method of claim 8, wherein the NH₂ group is protected causing the compound of formula III to react with a compound selected from the group of an organic acid of the formula R⁸COOH, an ester of the formula R⁸COOR⁹ in which R⁸ is an electron withdrawing group, an anhydride of the formula R⁸CO—O—COR⁹, an organic halide of the formula R⁸COX or di-tert-butyl di-tert-butyldicarbonate, in which R⁸, R⁹ independently of each other may be a hydrocarbon chain having 1–50 carbon atoms, a straight or a branched chain, saturated or containing one or more double bonds, cyclic, aromatic, containing one or more functional groups.

10. The method of claim 1 wherein in said elimination reaction the compound with an azide or N—BOC protected NH₂ group reacts with an aldehyde, a ketone or a silyl compound with at least two groups reactive with OH, to form a six membered ring with the C₁ and C₃ OH group.

11. The method of claim 1 wherein the compound of formula III reacts with an azide compound R⁵—N₃, in which R⁵ is an electron withdrawing group.

12. The method of claim 11, wherein the azide R⁵N₃ is a sulfonyl azide corresponding to the formula

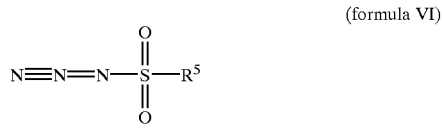

(formula VI)

wherein R⁵ is an electron withdrawing substituent, selected from an alkyl group having 1–6 carbon atoms, a halogen atom, a halogenated methyl or ethyl group, an aryl group, a phenyl group, or a phenyl group, or a phenyl group containing one or more substituents.

13. The method of claim 12, wherein the azide compound is generated in situ by reaction of a sulfonic anhydride

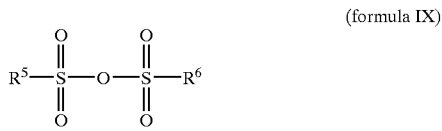

(formula IX)

with MN₃, wherein

M is a monovalent cation,

R⁵ and R⁶ are the same or different and are represented by alkyl group having 1–6 carbon atoms, a halogen atom, a halogenated methyl or ethyl group, an aryl group, a phenyl group, or a phenyl group containing one or more substituents.

14. The method of claim 13, wherein the sulfonyl azide generating compound is trifluoromethane sulphonic anhydride.

15. The method of claim 1 wherein in the removing of the NH₂ group the compound is sulfonylated by reacting the compound with an amount of a compound corresponding to formula IX

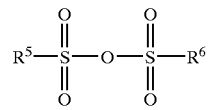

in which R⁵ and R⁶ are the same or different and are represented by alkyl group having 1–6 carbon atoms, a halogen atom, a halogenated methyl or ethyl group, an aryl group, a phenyl group, or a phenyl group containing one or more substituents.

16. The method of claim 8 wherein the compound with the carbamate protected $NH_2$ group is activated prior to said elimination reaction by converting the C-4 OH group to a sulfoxide, a sulphonyl residue comprising an electron withdrawing group coupled to the S, a halogen, a sulfoxide group, a S-peroxide group, a Se—R group, a CH—Se—R, or a CH—SeO—R group.

17. The method of claim 16, wherein in the removing of said $NH_2$ group the C-4 OH group is oxidized to provide a ketone, which is then subjected to a sulfonylation reaction in the presence of a compound of formula VII

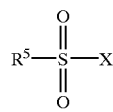

(formula VII)

to form a corresponding sulfonylated enol, wherein $R^5$ is an alkyl residue or an electron withdrawing group, and X is a halogen or a group corresponding to formula (VIII)

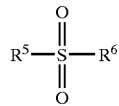

wherein $R^6$, independently of $R^5$, is an alkyl residue or an electron withdrawing group.

18. The method of claim 17, further comprising performing an elimination reaction on the sulfonylated enol in the presence of a catalyst selected from a Pd, Pt or Rh catalyst.

19. The method of claim 1 wherein said performing an elimination reaction comprises the step of reacting the compound of formula II with an organic acid, an activated ester, an acid halogenide, an acid anhydride, to convert the amine function to the corresponding amide.

20. The method of claim 19, wherein in the thus obtained amide, the NH group is caused to react with the C-1 OH group to form the corresponding oxazoline compound.

21. The method of claim 20, wherein the C-3 OH and C-4 OH are converted into a C-3-C-4 epoxide.

22. The method of claim 21 wherein before converting the C-3 OH and C-4 OH into a C-3-C-4 epoxide, the oxazoline compound is reacted with an amount of a compound corresponding to formula IX

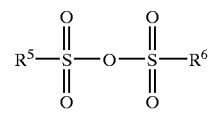

in which $R^5$ and $R^6$ are the same or different and are represented by alkyl group having 1–6 carbon atoms, a halogen atom, a halogenated methyl or ethyl group, an aryl group, a phenyl group, a phenyl group containing one or more substituents, to convert the C-4 OH group to a sulfonyl protected group.

23. The method of claim 22, wherein the epoxide is contacted with an electrophilic reactant, followed by contacting it with a nucleophilic reactant to open the epoxide and cause in this product the elimination reaction to take place by the addition of an organic base to form the C-4-C-5 double bond.

24. The method of claim 23, wherein the compound comprising the C-4-C-5 double bond, is subjected to a washing procedure in weak acid medium so as to open the oxazoline, followed by a washing procedure in strong alkaline medium to remove the $NH_2$ protecting group.

* * * * *